US008088786B2

(12) United States Patent
McKinney et al.

(10) Patent No.: US 8,088,786 B2
(45) Date of Patent: Jan. 3, 2012

(54) LAYERED PHARMACEUTICAL FORMULATIONS

(75) Inventors: Anthony McKinney, San Diego, CA (US); Gary Tollefson, Indianapolis, IN (US); Eckard Weber, San Diego, CA (US); Rick Soltero, Holly Springs, NC (US)

(73) Assignee: Orexigen Therapeutics, Inc., La Jolla, CA (US)

( * ) Notice: Subject to any disclaimer, the term of this patent is extended or adjusted under 35 U.S.C. 154(b) by 453 days.

(21) Appl. No.: 11/937,421

(22) Filed: Nov. 8, 2007

(65) Prior Publication Data

US 2008/0113026 A1 May 15, 2008

Related U.S. Application Data

(60) Provisional application No. 60/865,157, filed on Nov. 9, 2006.

(51) Int. Cl.
*A01N 43/42* (2006.01)
*A61K 31/44* (2006.01)

(52) U.S. Cl. .................................................... 514/279
(58) Field of Classification Search .................. 514/279
See application file for complete search history.

(56) References Cited

U.S. PATENT DOCUMENTS

| | | |
|---|---|---|
| 3,819,706 A | 6/1974 | Mehta |
| 3,885,046 A | 5/1975 | Mehta |
| 3,942,641 A | 3/1976 | Segre |
| 4,089,855 A | 5/1978 | Chatterjie et al. |
| 4,172,896 A | 10/1979 | Uno et al. |
| 4,218,433 A | 8/1980 | Kooichi et al. |
| 4,295,567 A | 10/1981 | Knudsen |
| 4,483,846 A | 11/1984 | Koide et al. |
| 4,513,006 A | 4/1985 | Maryanoff et al. |
| 4,673,679 A | 6/1987 | Aungst et al. |
| 4,689,332 A | 8/1987 | McLaughlin et al. |
| 4,831,031 A | 5/1989 | Lowe et al. |
| 4,855,306 A | 8/1989 | Markstein et al. |
| 4,895,845 A | 1/1990 | Seed |
| 5,028,612 A | 7/1991 | Glover |
| 5,082,864 A | 1/1992 | Van den Oetelaar et al. |
| 5,202,128 A | 4/1993 | Morella et al. |
| 5,213,807 A | 5/1993 | Chemburkar et al. |
| 5,213,808 A | 5/1993 | Bar-Shalom et al. |
| 5,283,263 A | 2/1994 | Norden |
| 5,312,925 A | 5/1994 | Allen et al. |
| 5,358,970 A | 10/1994 | Ruff et al. |
| 5,364,841 A | 11/1994 | Cooper et al. |
| 5,403,595 A | 4/1995 | Kitchell et al. |
| 5,426,112 A | 6/1995 | Zagon et al. |
| 5,427,798 A | 6/1995 | Ludwig et al. |
| 5,486,362 A | 1/1996 | Kitchell et al. |
| 5,512,593 A | 4/1996 | Dante |
| 5,541,231 A | 7/1996 | Ruff et al. |
| 5,626,874 A | 5/1997 | Conte et al. |
| 5,714,519 A | 2/1998 | Cincotta et al. |
| 5,716,976 A | 2/1998 | Bernstein |
| 5,719,197 A | 2/1998 | Kanios et al. |
| 5,731,000 A | 3/1998 | Ruff et al. |
| 5,738,874 A * | 4/1998 | Conte et al. .................. 424/472 |
| 5,763,493 A | 6/1998 | Ruff et al. |
| 5,817,665 A | 10/1998 | Dante |
| 5,856,332 A | 1/1999 | Dante |
| 5,866,164 A | 2/1999 | Kuczynski et al. |
| 5,958,962 A | 9/1999 | Cook |
| 5,977,099 A | 11/1999 | Nickolson |
| 6,004,970 A | 12/1999 | O'Malley et al. |
| 6,033,686 A | 3/2000 | Seth |
| 6,034,091 A | 3/2000 | Dante |
| 6,048,322 A | 4/2000 | Kushida |
| 6,071,537 A | 6/2000 | Shank |
| 6,071,918 A | 6/2000 | Cook |
| 6,087,386 A | 7/2000 | Chen et al. |
| 6,110,973 A | 8/2000 | Young |
| 6,150,366 A | 11/2000 | Arenson et al. |
| 6,153,223 A | 11/2000 | Apelian et al. |
| 6,183,778 B1 | 2/2001 | Conte et al. |
| 6,191,117 B1 | 2/2001 | Kozachuk |
| 6,197,827 B1 | 3/2001 | Cary |
| 6,210,716 B1 | 4/2001 | Chen et al. |
| 6,245,766 B1 | 6/2001 | Watsky |
| 6,248,363 B1 | 6/2001 | Patel et al. |
| 6,262,049 B1 | 7/2001 | Coffin et al. |

(Continued)

FOREIGN PATENT DOCUMENTS

CA         2317044         7/1999

(Continued)

OTHER PUBLICATIONS

Ackerman et al. 1998. Clinical characteristics of response to fluoxetine treatment of obsessive-compulsive disorder. Journal of Clinical Psychopharmacology, 18(3):185-192.

Altman et al. (2005) Standard Deviations and Standard Errors, BMJ, 331:903.

Anderson et al. (2002) Bupropion SR enhances weight loss, Obesity R., 10(7):633-641.

Appolinario et al. (2004) Pharmacological Approaches in the Treatment of Binge Eating Disorder, Current Drug Targets, 5:301-307.

Aronne et al. (2003) Weight gain in the treatment of mood disorders, J. Clin Psychiatry, 64(suppl 9).

Asconape, 2002, Some Common Issues in the Use of Antiepileptic Drugs, Seminars in Neurology; 22(1):27-39.

(Continued)

*Primary Examiner* — San-Ming Hui
*Assistant Examiner* — Kathrien Cruz
(74) *Attorney, Agent, or Firm* — Knobbe, Martens, Olson & Bear LLP

(57) ABSTRACT

In one embodiment a layered pharmaceutical formulation includes two or more pharmaceutical layers and an intermediate layer disposed between at least two of the two or more pharmaceutical layers, the intermediate layer configured to dissolve in vivo to thereby leave the two or more pharmaceutical layers substantially intact. In one embodiment, an active pharmaceutical ingredient in at least one of the pharmaceutical layers is selected from bupropion, zonisamide, naltrexone, topiramate, phentermine, metformin, olanzapine and fluoxetine.

6 Claims, 5 Drawing Sheets

U.S. PATENT DOCUMENTS

| | | |
|---|---|---|
| 6,274,579 B1 | 8/2001 | Morgan et al. |
| 6,294,192 B1 | 9/2001 | Patel et al. |
| 6,306,436 B1 | 10/2001 | Chungi et al. |
| 6,323,236 B2 | 11/2001 | McElroy |
| 6,342,496 B1 | 1/2002 | Jerussi et al. |
| 6,342,515 B1 | 1/2002 | Masuda et al. |
| 6,344,474 B1 | 2/2002 | Maruani et al. |
| 6,369,113 B2 | 4/2002 | Young |
| 6,383,471 B1 | 5/2002 | Chen et al. |
| 6,387,956 B1 | 5/2002 | Shapira |
| 6,420,369 B1 | 7/2002 | Marcotte |
| 6,437,147 B1 | 8/2002 | Andersen et al. |
| 6,441,038 B1 | 8/2002 | Loder et al. |
| 6,462,237 B1 | 10/2002 | Gidwani et al. |
| 6,500,459 B1 | 12/2002 | Chhabra et al. |
| 6,506,799 B1 | 1/2003 | Dasseux |
| 6,514,531 B1 | 2/2003 | Alaux et al. |
| 6,528,520 B2 | 3/2003 | Clemens |
| 6,541,478 B1 * | 4/2003 | O'Malley et al. ........ 514/252.15 |
| 6,548,551 B2 | 4/2003 | Hinz |
| 6,569,449 B1 | 5/2003 | Stinchcomb et al. |
| 6,576,256 B2 | 6/2003 | Liang et al. |
| 6,589,553 B2 | 7/2003 | Li et al. |
| 6,622,036 B1 | 9/2003 | Suffin |
| 6,627,223 B2 | 9/2003 | Percel et al. |
| 6,630,165 B2 | 10/2003 | Seroff et al. |
| 6,638,535 B2 | 10/2003 | Lemmens et al. |
| 6,652,882 B1 | 11/2003 | Odidi et al. |
| 6,682,759 B2 | 1/2004 | Lim et al. |
| 6,686,337 B2 | 2/2004 | Connor |
| 6,706,283 B1 | 3/2004 | Appel et al. |
| 6,713,488 B2 | 3/2004 | Sadee et al. |
| 6,797,283 B1 | 9/2004 | Edgren et al. |
| 6,893,660 B2 | 5/2005 | Li et al. |
| 6,893,661 B1 | 5/2005 | Odidi et al. |
| 6,905,708 B2 | 6/2005 | Li et al. |
| 6,923,988 B2 | 8/2005 | Patel et al. |
| 6,926,907 B2 | 8/2005 | Plachetka |
| 7,109,198 B2 | 9/2006 | Gadde et al. |
| 7,375,111 B2 | 5/2008 | Weber et al. |
| 7,422,110 B2 | 9/2008 | Zanden et al. |
| 7,425,571 B2 | 9/2008 | Gadde et al. |
| 7,429,580 B2 | 9/2008 | Gadde et al. |
| 7,462,626 B2 | 12/2008 | Weber et al. |
| 7,754,748 B2 | 7/2010 | Gadde et al. |
| 2001/0025038 A1 | 9/2001 | Coffin et al. |
| 2001/0046964 A1 | 11/2001 | Percel et al. |
| 2002/0012680 A1 | 1/2002 | Patel et al. |
| 2002/0019364 A1 | 2/2002 | Renshaw |
| 2002/0022054 A1 | 2/2002 | Sawada et al. |
| 2002/0025972 A1 | 2/2002 | Hinz |
| 2002/0037836 A1 | 3/2002 | Henriksen |
| 2002/0044962 A1 | 4/2002 | Cherukuri et al. |
| 2002/0055512 A1 | 5/2002 | Marin et al. |
| 2002/0090615 A1 | 7/2002 | Rosen et al. |
| 2002/0198227 A1 | 12/2002 | Bernstein |
| 2003/0003151 A1 | 1/2003 | Chopra |
| 2003/0017189 A1 | 1/2003 | Wong et al. |
| 2003/0035840 A1 | 2/2003 | Li et al. |
| 2003/0054031 A1 | 3/2003 | Li et al. |
| 2003/0054041 A1 | 3/2003 | Lemmens et al. |
| 2003/0055008 A1 | 3/2003 | Marcotte |
| 2003/0055038 A1 | 3/2003 | Howard et al. |
| 2003/0068371 A1 | 4/2003 | Oshlack et al. |
| 2003/0087896 A1 | 5/2003 | Glover |
| 2003/0091630 A1 | 5/2003 | Louie-Helm et al. |
| 2003/0109546 A1 | 6/2003 | Fenton |
| 2003/0130322 A1 | 7/2003 | Howard |
| 2003/0133982 A1 | 7/2003 | Heimlich et al. |
| 2003/0133985 A1 | 7/2003 | Louie-Helm et al. |
| 2003/0135056 A1 | 7/2003 | Andersen et al. |
| 2003/0144174 A1 | 7/2003 | Brenna et al. |
| 2003/0144271 A1 | 7/2003 | Shulman |
| 2003/0147952 A1 | 8/2003 | Lim et al. |
| 2003/0161874 A1 | 8/2003 | Li et al. |
| 2003/0198683 A1 | 10/2003 | Li et al. |
| 2003/0215496 A1 | 11/2003 | Patel et al. |
| 2004/0002462 A1 | 1/2004 | Najarian |
| 2004/0022852 A1 | 2/2004 | Chopra |
| 2004/0029941 A1 | 2/2004 | Jennings |
| 2004/0047908 A1 | 3/2004 | Lemmens et al. |
| 2004/0059241 A1 | 3/2004 | Suffin |
| 2004/0092504 A1 | 5/2004 | Benja-Athon |
| 2004/0096499 A1 | 5/2004 | Vaya et al. |
| 2004/0101556 A1 | 5/2004 | Li et al. |
| 2004/0105778 A1 | 6/2004 | Lee et al. |
| 2004/0106576 A1 | 6/2004 | Jerussi et al. |
| 2004/0115134 A1 | 6/2004 | Merisko-Liversidge |
| 2004/0122033 A1 | 6/2004 | Nargund et al. |
| 2004/0158194 A1 | 8/2004 | Wolff et al. |
| 2004/0185097 A1 | 9/2004 | Kannan et al. |
| 2004/0204472 A1 | 10/2004 | Briggs et al. |
| 2004/0228915 A1 | 11/2004 | Noack et al. |
| 2004/0242974 A1 | 12/2004 | Glover |
| 2004/0254208 A1 | 12/2004 | Weber et al. |
| 2004/0258757 A1 | 12/2004 | Bosch et al. |
| 2005/0004106 A1 | 1/2005 | Romano |
| 2005/0013863 A1 | 1/2005 | Lim et al. |
| 2005/0019385 A1 | 1/2005 | Houze |
| 2005/0019409 A1 | 1/2005 | Edgren et al. |
| 2005/0019412 A1 | 1/2005 | Bosch et al. |
| 2005/0026977 A1 | 2/2005 | Jennings |
| 2005/0026986 A1 | 2/2005 | Maruani et al. |
| 2005/0031691 A1 | 2/2005 | McGurk et al. |
| 2005/0043704 A1 | 2/2005 | Lieberburg |
| 2005/0043705 A1 | 2/2005 | Lieberburg |
| 2005/0043773 A1 | 2/2005 | Lieberburg |
| 2005/0063913 A1 | 3/2005 | Pruitt et al. |
| 2005/0096311 A1 | 5/2005 | Suffin et al. |
| 2005/0112198 A1 | 5/2005 | Challapalli et al. |
| 2005/0112211 A1 | 5/2005 | Gervais et al. |
| 2005/0118268 A1 | 6/2005 | Percel et al. |
| 2005/0137144 A1 | 6/2005 | Gadde et al. |
| 2005/0142195 A1 | 6/2005 | Li et al. |
| 2005/0143322 A1 | 6/2005 | Gadde et al. |
| 2005/0147664 A1 | 7/2005 | Liversidge et al. |
| 2005/0154002 A1 | 7/2005 | Crooks et al. |
| 2005/0163840 A1 | 7/2005 | Sawada et al. |
| 2005/0181049 A1 | 8/2005 | Dong et al. |
| 2005/0214368 A1 | 9/2005 | Kawakami et al. |
| 2005/0214371 A1 | 9/2005 | Di Capua et al. |
| 2005/0214372 A1 | 9/2005 | Di Capua et al. |
| 2005/0215552 A1 | 9/2005 | Gadde et al. |
| 2005/0232990 A1 | 10/2005 | Boehm et al. |
| 2005/0238718 A1 | 10/2005 | Oberegger et al. |
| 2005/0245460 A1 | 11/2005 | Meyerson et al. |
| 2005/0250838 A1 | 11/2005 | Challapalli et al. |
| 2005/0277579 A1 | 12/2005 | Gadde et al. |
| 2006/0009514 A1 | 1/2006 | Gadde et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0058293 A1 | 3/2006 | Weber et al. |
| 2006/0069086 A1 | 3/2006 | Michalow |
| 2006/0079501 A1 | 4/2006 | Gadde et al. |
| 2006/0100205 A1 | 5/2006 | Weber et al. |
| 2006/0122127 A1 | 6/2006 | Rao et al. |
| 2006/0142290 A1 * | 6/2006 | Weber et al. ............... 514/238.8 |
| 2006/0160750 A1 | 7/2006 | Gadde et al. |
| 2006/0246131 A1 | 11/2006 | Cottinham |
| 2006/0276412 A1 | 12/2006 | Tollefson |
| 2007/0078135 A1 | 4/2007 | Yuan et al. |
| 2007/0117827 A1 | 5/2007 | Tollefson et al. |
| 2007/0128298 A1 | 6/2007 | Cowley et al. |
| 2007/0129283 A1 | 6/2007 | McKinney et al. |
| 2007/0148237 A1 | 6/2007 | McKinney et al. |
| 2007/0149451 A1 | 6/2007 | Holmes |
| 2007/1048237 | 6/2007 | McKinney et al. |
| 2007/0179168 A1 | 8/2007 | Cowley et al. |
| 2007/0185084 A1 | 8/2007 | McKinney et al. |
| 2007/0270450 A1 | 11/2007 | Weber et al. |
| 2007/0275970 A1 | 11/2007 | Weber et al. |
| 2007/0281021 A1 | 12/2007 | McKinney et al. |
| 2008/0027487 A1 | 1/2008 | Patel et al. |
| 2008/0110792 A1 | 5/2008 | McKinney et al. |
| 2008/0214592 A1 | 9/2008 | Cowley et al. |
| 2009/0018115 A1 | 1/2009 | Gadde et al. |

| | | | |
|---|---|---|---|
| 2009/0076108 | A1 | 3/2009 | Gadde et al. |
| 2010/0190793 | A1 | 7/2010 | Weber et al. |
| 2011/0059170 | A1 | 3/2011 | McKinney et al. |
| 2011/0098289 | A1 | 4/2011 | Gadde et al. |
| 2011/0144145 | A1 | 6/2011 | Tollefson |
| 2011/0172260 | A1 | 7/2011 | Dunayevich et al. |

FOREIGN PATENT DOCUMENTS

| | | |
|---|---|---|
| EP | 0 005 636 | 11/1979 |
| EP | 0 294 028 | 12/1988 |
| EP | 0 442 769 | 8/1991 |
| EP | 0 541 192 | 5/1993 |
| EP | 1 275 373 | 1/2003 |
| EP | 1 759 701 | 7/2007 |
| RU | 2214241 | 10/2003 |
| WO | WO 83/03197 | 9/1983 |
| WO | WO 90/13294 | 11/1990 |
| WO | WO 94/20100 | 9/1994 |
| WO | WO 96/09047 | 3/1996 |
| WO | WO 97/41873 | 11/1997 |
| WO | WO 98/00130 | 1/1998 |
| WO | WO 99/37305 | 7/1999 |
| WO | WO 99/38504 | 8/1999 |
| WO | WO 00/50020 | 8/2000 |
| WO | WO 00/51546 | 9/2000 |
| WO | WO 00/61139 | 10/2000 |
| WO | WO 00/62757 | 10/2000 |
| WO | WO 00/76493 A | 12/2000 |
| WO | WO 01/01973 | 1/2001 |
| WO | WO 01/26641 | 4/2001 |
| WO | WO 01/52851 | 7/2001 |
| WO | WO 01/58451 | 8/2001 |
| WO | WO 01/62257 | 8/2001 |
| WO | WO 01/78725 | 10/2001 |
| WO | WO 01/85257 | 11/2001 |
| WO | WO 02/09694 | 2/2002 |
| WO | WO 02/24214 | 3/2002 |
| WO | WO 02/087590 | 11/2002 |
| WO | WO 03/013524 | 2/2003 |
| WO | WO 03/092682 | 11/2003 |
| WO | WO 03/097046 A | 11/2003 |
| WO | WO 03/097051 | 11/2003 |
| WO | WO 2004/002463 | 1/2004 |
| WO | WO 2004/009015 | 1/2004 |
| WO | WO 2004/024096 | 3/2004 |
| WO | WO 2004/054570 | 7/2004 |
| WO | WO 2004/071423 | 8/2004 |
| WO | WO 2004/091593 | 10/2004 |
| WO | WO 2004/100956 | 11/2004 |
| WO | WO 2004/100992 | 11/2004 |
| WO | WO 2004/110368 | 12/2004 |
| WO | WO 2004/110375 | 12/2004 |
| WO | WO 2005/000217 | 1/2005 |
| WO | WO 2005/077362 | 2/2005 |
| WO | WO 2005/032555 | 4/2005 |
| WO | WO 2005/049043 | 6/2005 |
| WO | WO 2005/070641 | 8/2005 |
| WO | WO 2005/079773 | 9/2005 |
| WO | WO 2005/089486 | 9/2005 |
| WO | WO 2006/049941 | 5/2006 |
| WO | WO 2006/052542 | 5/2006 |
| WO | WO 2006/055854 | 5/2006 |
| WO | WO 2006/088748 A | 8/2006 |
| WO | WO 2007/012064 | 1/2007 |
| WO | WO 2007/047351 | 4/2007 |
| WO | WO 2007/145863 A | 12/2007 |

OTHER PUBLICATIONS

Astrup et al. (Mar. 1991) Thermogenic Synergism Between Ephedrine and Caffiene in Healthy Volunteers: A Double-Blind, Placebo-Controlled Study, Metabolism, 40(3):323-329.

Atkinson (2003) Clinical Guidelines on the identification, Evaluation, and pharamacologic treatment of obesity in Adults, Online, 07-25, URL:http://www.endotext.org.obesity/obesity15b/obesity15b.htm.

Atkinson et al. (Oct. 1985) Effects of long-term therapy with naltrexone on body weight in obesity, Clinical Pharmacology & Therapeutics, 38:419-422.

Ayala (2000) Weight Loss Associated With the Administration of Zonisamide, AES Proceedings, Epilepsia 41(Suppl. 7):99—No. 2.041.

Ayala et al., Dec. 1-6, 2000, Weight loss associated with the adminsitraiton of zonisamide, a compendium of posters and platform sessionf ro Zonegran™ and Diastat®, Annual Meeting 2000 of the American Epilepsy Society, Los Angeles, CA.

Baldassano et al. (2006) Acute treatment of bipolar depression with adjunctive zonisamide: a retrospective chart review, Disorders 6:432-434.

Barr et al. 1993. The serotonin hypothesis of obsessive compulsive disorder. International Clinical Psychopharmacology, 8(2):79-82.

Bastani et al. 1991. Serotonin uptake and imipramine binding in the blood platelets of obsessive-compulsive disorder patients. Biol. Psychiatry, 30:131-139.

Beelen et al. (2001) Asymptomatic QTC prolongation associated with queitiapine fumarate overdose in a patient being treated with risperidone, Human & Experimental Toxicology 20:215-219.

Benjamin et al. 1993. Naltrexone and fluoxetine in Prader-Willi syndrome. J. Am. Acad. Child Adolesc. Psychiatry, 32(4):870-873.

Bergeron et al. 2002. Sertraline and fluoxetine treatment of obsessive-compulsive disorder: Results of a double-blind, 6-month treatment study. Journal of Clinical Psychopharmacology, 22(2):148-154.

Berke et al. (Jul. 15, 2000) Medical Management of Obesity, American Academy of Family Physicians, 62(2):419-26 Abstract.

Billett et al. 1997. Obsessive compulsive disorder, response to serotonin reuptake inhibitors and the serotonin transporter gene. Molecular Psychiatry, 2:403-406.

Blanchard et al. (2003) Pancreatitis Treated with Didanosine and Tenofabir Disoproxil Fumarate Clinical Infectious Diseases, 37:57-62.

Broocks et al. 1998. Higher prevalence of obsessive-compulsive symptoms in patients with blepharospasm than in patients with hemifacial spasm. Am. J. Psychiatry, 155:555-557.

Bupropion (Oral Route), MayoClinic.com, 19 pp., 2009.

Calabrese et al. (Sep. 2000) Letters to the Editors, Lamotrigine and Clozapine for Bipolar Disorder, American J. of Psychiatry, 157:1523.

Carlsen et al. (Jan. 1998) Evidence for dissociation of insulin-and weight-reducing effects of metformin in non-diabetic male patients with coronary heart disease, Diabetes Research and Clinical Practice Amersterdam, 39(1):47-54.

Carpenter et al. (Jan. 1, 1999) Mirtazapine Augmentation in the Treatment of Refractory Depression, J Clin Psychiatry, 60:1.

Carrion, 1995. Naltrexone for the treatment of trichotillomania: A case report. J. Clin. Psychopharmacol., 15(6):444-445.

Carroll (2003) Medicinal Chemistry Division Award Address: Monoamine Transporters and Opioid Receptors. Targets for Addiction Therapy, J. Med. Chem; 46(10)1775-1794.

Carter et al. 2003. Pharmacologic treatment of binge-eating disorder. Primary Psychiatry, 10(10)31-36.

Cash et al. (2000) Attitudes about antidepressants: Influence of information about weight-related side effects, Perceptual and Motor Skills, 90:453-456.

Casner et al. 1996. Naltrexone and self-injurious behavior: A retrospective population study. Journal of Clinical Psychopharmacology, 16(5):389-394.

Chen et al. (Jan. 2004) Synergistic Effects of Cannabiniod inverse agonist AM251 and opiod antagonist namefene on food intake, Brain Res, 999:22-230.

Chengappa et al. (2002) Changes in body Weight and Body mass index among psychiatric patients receiving lithium, valproate, or topiramate: an open-label, nonrandomized chart review, Clinical Therapeutics, 24(10):1576-1584.

Ching, Mar. 1980, Influence of diphenylhydantoin upon oral glucose tolerance test in obesity, Chinese Medical Journal, 27(1):432-439.

Chouinard et al. 1996. Potentiation of fluoxetine by aminoglutethimide, an adrenal steriod suppressant, in obsessive-compulsive disorder resistant to SSRIs: A case report. Prog. Neuro-Psychopharmacol. & Biol. Psychiat., 20:1067-1079.

Clapham et al. (2001) Anti-obesity drugs: a critical review of current therapies and future opportunities. Pharmacoloty & Therapeutics. 89:81-121.

Clark et al., 2003, Diabetes mellitus associated with atypical antipsychotic medications, Diabetes Technology & Therapeutics, 5(4):669-683.

Clinical Trial: Drug Treatment for Depressed Alcoholics (Naltrexone/Fluoxetine). (n.d.) Retrieved Jun. 28, 2007, from http://www.clinicaltrials.gov/ct/show/NCT00006204;jsessionid+FED6D0856E098BC0B1940E464179B71B?order=28.

Colosimo, et al. 1999. Motor fluctuations in Parkinson's disease: Pathophysiology and treatment. European Journal of Neurology, 6:1-21.

Cone et al. (2001) The arcuate nucleus as a conduit for diverse signals relevant to energy homeostasis, Int'l Journal of Obesity, 25(5):S63-S67.

Croft et al. (Apr. 2002) Effect on body weight of bupropion sustained-release in patients with major depresssion treated for 52 weeks, Clinical Therapeutics 24(4):662-672.

Dechant et al. (1991) Drugs, 41:225-253.

Dembowski et al. (2003) Successful Antimanic Treatment and Mood Stabilization with Lamotrigine, Clozapine, and Valproate in a Bipolar Patient after Lithium-induced Cerebellar Deterioration, Letter Pharmacopsychiatry, 36:83-86.

Deshmukh et al. (Jul. 2003) Managing weight gain as a side effect of antidepressant therapy, Cleveland Clinic Journal of Medicine, vol. 70.

DeSimone et al. (2005) Carbonic anhydrase inhibitors. Zonisamide is an effective inhibitor of the cytosolic isozyme II and mitochondrial isozyme V: Solution and x-ray crystallographic studies, Bioorganic & Medicinal Chemistry Letters, 15:2315-2320.

Devlin et al. (2000) Open treatment of overweight binge eaters with phentermine and fluoxetine as an adjunct to cognitive-behavioral therapy. Int. J. Eating Disord; 28:325-332.

Sleep Disorders, in Diagnostic and Statistical Manual of Mental Disorders, 4$^{th}$ Edition, American Psychiatric Association, p. 583-595 (2000).

Dursen et al. (Oct. 1999) Clozapine Plus Lamotrigine in Treatment-Resistant Schizophrenia, Arch Gen Psychiatry, 56:950-951.

Dursun et al. (2001) Accelerated Weight Loss After Treating Refractory Depression with Fluoxetine Plus Topiramate: Possible Mechanism of Action, Canadian Journal of Psychiatry, 46(3):287-288.

Dursun et al. (2001) Augmenting Antipsychotic treatment with Lamotrigine or topiramate in patients with treatment-resistant Schizophrenia: a naturalistic case-series outcome study Journal of Psychopharmacology 15(4):297-301.

Dursun et al. (2001) Psychopharmacology for the Clinician Psychopharmacologie Pratiqu, Journal of Psychiatry Neuroscience, 26(2):168.

Dursun et al. (Winter 2002) Lamotrgine-Clozapine Combination in Refractory Schizophrenia: Three Cases, J. Neuropsychiatry Clin. Neuroscience, 14:1:86.

Dwyer et al., 2002, Psychoactive drugs affect glucose transport and the regulation of glucose metabolism, International Review of Neurobiology, 51:503-530.

El-Haschimi et al. 2000. Two defects contribute to hypothalamic leptin resistance in mice with diet-induced obesity. The Journal of Clinical Investigation, 105(12):1827-1832.

Erez et al., 1982, Narcotic antagonistic potency of bivalent ligands which contain β-naltrexamine. Evidence for bridging between proximal recognition sites, J. Med. Chem., 25:847-849.

Erfuth et al. (Mar. 2002) Bupropion as add-on strategy in difficult-to-treat bipolar depressive patients, Neurophsychobiology, 45(Supplement 1):33-36.

Erzegovesi et al. 2001. Clinical predictors of drug response in obsessive-compulsive disorder. Journal of Clinical Psychopharmacology, 21(5):488-492.

Esposito-Avella et al. (Jan. 1973) Studies on the protective effect of diphenylhyndantoin against alioxan diabetes in mice, Proceedings of the Society for Experiemental Biology & Medicine, 142(1):82-85.

Ettmayer et al, May 6, 2004, Lessons learned from marketed and investigational prodrugs, J. Med. Chem, 47(10):2393-2404.

Faught et al. (2001) Randomized Controlled Trial of Zonisamide for the Treatment of Refractory Partial-Onset Seizures., Neurology; 57(10):1774-1779.

Fava, Maurizio (2000) Weight Gain and Antidepressants. J Clin Psychiatry; 61(suppl 11):37-41.

Ferre et al. (1996) Correction of diabetic alterations by glucokinase. Proc. Natl. Acad. Sci. USA, 93:7225-7230.

Ferre et al. (1996) Evidence from transgenic mice that glucokinase is rate limiting for glucose utilization in the liver, The FASEB Journal, 10:1213-1218.

Fingl et al., The Pharmacological Basis of Theraputics. Chapter 1: General Principles, pp. 1-46 (1975).

Fontela et al., Mar. 1986, Blocking effect of naloxone, dihydroergotamine and adrenalectomy in lithium-induced hyperglycaemia and glucose intolerance in the rate, Acta Endocrinologica, 111(3):342-348 (abstract).

Fukagawa et al. (Nov. 2001) Monoaminergic anorectic agents, Nippon Yikurigaku Zasshi, 118(5):303-8, 2001 Abstract.

Fulghesu et al. (Aug. 1993) Long-term naltrexone treatment reduces the exaggerated insulin secretion in patients with polycystic ovary disease, Obstetrics & Gynecology, 82(2):191-197.

Fuller et al. (1989) Fluoxetine: A Serotonergic Appetite Suppressant Drug, Drug Development Research, 17(1):1-15.

Gadde et al., 2002, Randomized controlled trial of zonisamide for treating obesity, Epilepsia 43 Suppl. 7:218 (abstract).

Gadde et al, "Zonisamide in Obesity: A 16-Week Randomized Trial", No. NR473, New Research, American Psychiatric Association 2002 Annual Meeting, May 18-23, 2002, Philadelphia, Pennsylvania (abstract).

Gadde et al, Randomized Trial of Weight Loss Efficacy of Zonisamide, No. 304, 26(Suppl. 1), Journal of the International Association for the Study of Obesity, Ninth International Congress on Obesity, Sao Paolo, Brazil, Aug. 24-29, 2002.

Gadde et al. "Bupropion for Weight Loss: An Investigation of Efficacy and Toleability in Overweight and Obese Women" Obesity Reseach 9 (9): 544-551 (2001).

Gadde et al. (2003) Zonisamide enhances weight loss in patients with obesity. Inpharma; 1383/84:9.

Gadde et al. , "Zonisamide for Weight Loss in Obese Adults—A Randomized Controlled Trial" JAMA 289 (14): 1820-1825 (2003).

Gadde et al., May 1999, Bupropion Sustained Release in Obesity: A Randomized Double-Blind, Placebo-Controlled Study, No. NR634, New Research Program & Abstracts, American Psychiatric Association, 1999 Annual Meeting, The Clinician, Washington, D.C.

Gadde et al., Sep. 1999, A randomized double-blind placebo-controlled study of bupropion sustained release in obesity, European Neuropsychopharmacology, 9(5):366.

Gatley et al. (1996) $^{123}$I-labeled AM251: a radioiodinated ligand which binds in vivo to mouse brain cannabinoid $CB_1$ receptors. European Journal of Pharmacology; 307:331-338.

Gehlert et al. (Oct. 1998) The Selective Norepinephrine Reuptake Inhibitor, LY368975, Reduces Food Consumption in Animal Models of Feeding, J. Pharmacology and Experimental Therapeutics, 87(1):122-7 Abstract.

Gerich et al. (1972) In vitro inhibition of pancreative glucagon secretion by diphenylhydantoin, Journal of Clinical Endocrinology and Metabolism 35(6):823-823.

Gerra et al. 1995. Hostility in heroin abusers subtypes: Fluoxetine and naltrexone treatment. Prog. Neuro-Psychopharmacol. & Biol. Psychiat., 19:1225-1237.

Gerra et al., Sep. 30, 2006, Effects of olanzapine on aggressiveness in heroin dependent patients, Progress in Neuro-Psychopharmacology & Biological Psychiatry, 30(7):1291-1298.

Ginsberg et al. (2000) Effects of Mood Stabilizers on Weight, Primary Psychiatry 7(5):49-58.

Givens et al. (1987) Reduction of hyperinsulinemia and insulin resistance by opiate receptor blockade in the polycystic ovary syndrome with acanthosis nigricans, Journal of Clinical Endocrinology and Metabolism, 64(2):377-382.

Glass et al. (1999) Opioids and food intake: distributed functional neural pathways? Neuropeptides; 33(5):360-368.

Grunenthal, Neo-Eunomin Gebrauchsinformation, Neo-Eunomin Prescription Information, Feb. 2004, pp. 1-2.

Goldstein et al. (Mar. 1994) Fluoxetine: a randomized clinical trial in the treatment of obesity, International Journal of Obesity and Related Metabolic Disorders, 17(3):129-135, CAS accession #9424430.

Goodman et al. 1989. The Yale-Brown obsessive compulsive scale. Arch. Gen. Psychiatry, 46:1006-1011.

Gordon et al. (Jun. 1999) Mood Stablization and Weight Loss with Topiramate American Journal of Psychiatry, American Psychiatric Association, Washington D.C., 156(6):968-969.

Grady (Mar. 15, 2003) Quest for Weight-Loss Drug Takes an Unusual Turn, The New York Times—Health, www.nytimes.com, 3 pp.

Grant et al. 2004. Impulse control disorders: Clinical characteristics and pharmacological management. Annals of Clinical Psychiatry, 16:27-34.

Grant et al. 2004. Pharmacotherapy outcome in older pathological gamblers: A preliminary investigation. Journal of Geriatric Psychiatry and Neurology, 17(1):9-12.

Grant et al. 2006. Compulsive aspects of impulse-control disorders. Psychiatr. Clin. North Am., 29(2):539-x.

Greenberg et al. 1998. Delayed obsessive-compulsive disorder symptom exacerbation after a single dose of a serotonin antagonist in fluoxetine-treated but not untreated patients. Psychopharmacology, 140:434-444.

Greenway et al. (2000) A Long-acting Leptin Analog does not Enhance Fat, Visceral Fat, or Weight Loss When Combined with Caffeine Ephedrine in Obese Subjects, International Journal of Obesity, S136.

Greenway et al. (Jul. 1999) Double-Blind, Randomized, Placebo-Controlled Clinical Trials with Non-prescription Medications for the Treatment of Obesity, Obesity Research, 7(4):370-78.

Greist et al. (Apr. 1995) Double-blind Parallel Comparison of Three Dosages of Sertraline and Placebo in Outpatients With Obsessive-compulsive Disorder, Arch Gen Psychiatry, 52:289-295.

Hahn et al. (1985) Irreversible opiate agonists and antagonists. III. Phenylhydrazone derivatives of naloxone and oxymorphone. J. Pharm. Exper. Therapeutics; 235:846-850.

Hamidi et al. 2007. Naltrexone in obsessive-compulsive disorder: An open- label trial. Iranian Journal of Psychiatry and Behavioral Sciences, 1(1):16-21.

Harrison's Principles of Internal Medicine. Eleventh Edition, McGraw-Hill Book Company, pp. 1921-1930 (1987).

Hashiguti et al. (1993) Simultaneous determination of in vivo hydroxylation of tyrosine and tryptophan in rat striatum by microdialysis-HPLC: relationship between dopamine and serotonin biosynthesis; Journal of Neural Transmission, 93:213-223.

Hollander et al. 1991. Effects of chronic fluoxetine treatment on behavioral and neuroendocrine responses to meta-chloro-phenylpiperazine in obsessive-compulsive disorder. Psychiatry Research, 36:1-17.

Hussey et al., 2002, Synthesis of a β-estradiol-biotin chimera that potently heterodimerizes estrogen receptor and streptavidin proteins in a yeast three-hybrid system, J. Am. Chem. Soc., 125:3692-3693.

Insulin Resistance and Pre-diabetes, http://diabetes.niddk.hih.gov/DM/pubs/insulineresistance/, NIH Publication No. 09/4893, Oct. 2008, 9 pp.

Islam et al., 1994, Naltrexone, Serotonin Receptor Subtype Antagonists, and Carbohydrate Intake in Rats, Pharmacology Biochemistry and Behavior, 48(1):193-201.

Jain et al. (Oct. 2002) Bupropin SR vs. Placebo for Weight Loss in Obese Patients with Depressive Symptoms, Obesity Research, 10:1049-56.

Jallon et al. (2001) Bodyweight gain and anticonvulsants: a comparative review. Drug Safety; 24(13):969-978.

Japanese Journal of Clinical Psychiatry (1987 16(1):123-132), and English-language version of Japanese Office Action citing the same (dated Oct. 28, 2008).

Kanba et al. (1994) The first open study of zonisamide, a novel anticonvulsant, shows efficacy in mania. Progress in Neuro-Psychopharmacology and Biological Psychiatry; 18(4):707-715.

Kim et al. 1990. Open fixed dose trial of fluoxetine in the treatment of obsessive compulsive disorder. Drug Development Research, 19:315-319.

Kimura et al., 1992, Pharmacokinetic interaction of zonasamide in rats: effects of other antiepileptics on zonisamide, J. Pharmacobio-Dyn. 15:631-639.

Kiptoo et al. (2006) Enhancement of Transdermal delivery or 6-B-naltrexol via a codrug linked to hydroxyburpropion, Journal of Controlled Release 113:137-145.

Kirkham et al. (2001) Synergistic effects of opioid and cannabinoid antagonists on food intake. Psychopharmacology; 153:267-270.

Kirov et al. (2003) Add-on topiramate reduces weight in overweight patients with affective disorders: a clinical case. BMC Psychiatry, 5:19, 8 pp.

Klok et al., 2002, Cholesteryl-(l-lactic acid)n building blocks for self-assembling biomaterials, Macromolecules, 35:746-759.

Kolb et al. (1985) Synthesis and Pharmacological Characterization of Fluorescent Opioid Receptor Probes. A. Pharmaceutical Res, 2(6):266-271.

Korner et al. (2003) The emerging science of body weight regulation and its impact on obesity treatment, J. Clin. Invest. 111(5):565-570.

Kossard, et al. 2006. Defining urticarial dermatitis: A subset of dermal hypersensitivity reaction pattern. Arch. Dermatol., 142:29-34.

Krauss et al., 1997, Tics secondary to craniocerebral trauma, Movement Disorders, 12(5):776-782.

Krupitsky et al. 2006. Naltrexone with or without fluoxetine for preventing relapse to heroin addictbn in St. Petersburg, Russia. Journal of Substance Abuse Treatment, 31:319-328.

Kushner et al. (Mar. 2002) Obesity pharmacology: past, present, and future, Current Opinion in Gastroenterology, pp. 213-220.

Landabaso et al. 1998. A randomized trial of adding fluoxetine to a naltrexone treatment programme for heroin addicts. Addiction, 93(5):739-744.

Le Bourdonnec et al. (2000) J. Med. Chem., 43:2489-2492.

Leppik (Dec. 2004) Zonisamide: chemistry, mechanism of action, and pharmacokinetics, Seizure, 13(Suppl 1):S5-9; discussion S10.

Leppik et al. (1993) Efficacy and safety of zonisamide: results of a multicenter study. Epilepsy Research; 14:165-173.

Lesch et al. 1991. Long-term fluoxetine treatment decreases 5-HT1A receptor responsivity in obsessive-compulsive disorder. Psychopharmacology, 105:415-420.

Lessig et al. (Dec. 2001) Topiramate for Reversing Atypical Antipsychotic Weight Gain, J. Am. Child Adolesc. Psychiatry 40(12):1364.

Levy et al. (Nov. 2002) Topiramate Produced Weight Loss Following Olanzapine-Induced Weight Gain in Schizophrenia, J. Clin. Psychiatry, 63(11):1045.

Levy et al. 1985. Utility of free level monitoring of antiepileptic drugs. Epilepsia, 26(3):199-205.

Lin et al. 2000. Development of high fat diet-induced obesity and leptin resistance in C57B1/6J mice. International Journal of Obesity, 24:639-646.

López-Ibor, Jr. et al. 1996. Double-blind comparison of fluoxetine versus clomipramine in the treatment of obsessive compulsive disorder. European Neuropsychopharmacology, 6:111-118.

Malcolm et al. (Jun. 1985) A Controlled Trial of Naltrexone in Obese Humans, International Journal of Obesity, 9:347-353.

Malhotra et al. (2002) Medical Management of Obesity Associated With Mental Disorders, Journal of Clinical Psychiatry, 63(suppl 4):24-32.

Matsuura (2000) Indication for Anterior Temporal Lobectomy in Patients with Temporal Lobe Epilepsy and Psychopathology, Epilepsia, 41(Suppl. 9):39-42.

McDougle et al. (Aug. 2000) A double-blind, placebo-controlled study of risperidone addition in serotonin reuptake inhibitor-refractory obsessive-compulsive disorder, Archive of General Psychiatry, 57(8):794-801.

McElroy et al. (2000) Pharmacologic agents for the treatment of acute bipolar mania, Biological Psychiatry, 48(6):539-557.

McElroy et al. (2004) Zonisamide in the Treatment of Binge-Eating Disorder: An Open-Label, Prospective Trial, J. Clin. Psychiatry, 65(1):50-56.

McElroy et al. (2004) Zonisamide is effective in the treatment of binge-eating disorder. Inpharma; 1428:10.

McLaughlin et al. (2003) The cannabinoid CB1 antagonists SR 141716A and AM 251 suppress food intake and food-reinforced behavior in a variety of tasks in rats. Behavioral Pharmacology; 14:583:588.

Michelson et al. (Nov. 2001) Atomexetine in the Treatment of Children and Adolescents with Attention Deficit/Hyperactivity Disorder: A Randomized, Placebo-Controlled, Dose-Response Study, Pediatrics,108(5):E83 Abstract.

Millet et al. 1999. Obsessive-compulsive disorder: Evaluation of clinical and biological circadian parameters during fluoxetine treatment. Psychopharmacology, 146:268-274.

Mitchell et al. (1987) High-Dose Naltrexone Therapy and Dietary Counseling for Obesity, Biological Psychiatry, 22:35-42.

Monteleone et al. 1995. Plasma melatonin and cortisol cirdadian patterns in patients with obsessive-compulsive disorder before and after fluoxetine treatment. Psychoneuroendocrinology, 20(7):763-770.

Morris, III (Dec. 3, 2000) The Effect of Zonisamide Administration on Patient Weight, A Scientific Exhibit at the American Epilepsy Society Annual Meeting, Los Angeles, California.

Must et al. (Oct. 27, 1999) The disease burden associated with overweight and obesity, JAMA, 282(16):1523-1529.

Najim et al., Dec. 1, 1993, Role of endorphins in benzodiazepine-induced hyperglycaemia in mice, Pharmacology Biochemistry and Behavior, 46(4):995-997.

Naltrexone (Oral Route), MayoClinic.com, 11 pp., 2009.

Nash et al., Jul. 1, 2004, Anxiety disorders, Medicine, 32(7):17-21.

NIH Publication No. 05-3892, Dec. 2004, National Diabetes Statistics, 18 pp.

Navarro et al. (Jun. 2001) Topiramate for Clozapine-Induced Seizures, Am. J. Psychiatry, 158(6):968-969.

NDA 20-711, Approval Letter of Application No. NDA 20-711, Department of Health and Human Services, May 14, 1997, 3 pp.

NDA20-789, Zonegran (zonisamide) Capsules 100 mg, FDA Approved Labeling Text, p. 1-24 (Mar. 27, 2000).

Neumeister et al. 1999. Addition of naltrexone to fluoxetine in the treatment of binge eating disorder. Am. J. Psychiatry, 156(5):797.

Ninan et al., 1992, An improved synthesis of noroxymorphont, Tetrahedron., 48(32):6709-6716.

Niswender et al. 1997. Effects of increased glucokinase gene copy number on glucose homeostatis and hepatic glucose metabolism. The Journal of Biological Chemistry, 272(36):22570-22575.

Note for guidance on stability testing of existing active substances and related finished product, Committee for Proprietary Medicinal Products (CPMP), Apr. 22, 1998, 9 pp.

Novi et al. (Apr.-Jun. 1990) The role of opioid antagonists in the treatment of obesity. Results of a clinical trial with naltrexone, Minerva Endocrinol. 15(2):121-3, Abstract.

O'Byrne et al., Jan. 1, 1990, Effects of drugs on glucose tolerance in non-insulin-dependent diabetes (part II), Drugs, Adis International Ltd., 40(2):204-219.

Okada et al. (1992) Effects of zonisamide on extracellular levels of monoamine and its metabolite, and on Ca2+ dependent dopamine release Epilepsy Research, 13:113-119.

Okada et al. (1995) Effects of zonisamide on dopaminergic system, Epilepsy Research, 22:198-205.

Olsen et al., (1990) Conjugate Addition Ligands of Opioid Antagonists. Methacrylate Esters and Ethers of 6Alpha- and 6Beta-Naltrexol, Journal of Medicinal Chemistry, American Chemical Society, 33(2):737-741.

Olszewski et al. (Jun. 13, 2001) Evidence of Interactions Between Melanocortin and Opioid Systems in Regulation of Feeding, Neuroreort, 12(8):1727-1730.

Oommen et al. (1999) Zonisamide: A new antiepileptic drug. Clinical Neuropharmacology, 22(4):192-200.

Ortho-Novum Tablets and Modicon Tablets Prescribing Information, Apr. 2002, 8 pp.

Otake et al. (May 15, 2005) Association of visceral fat accumulation and plasma adiponectin and colorectal ademona: evidence for participation of insulin resistance, Clinical Cancer Research 11:3642-3646.

Ovadia, Oct. 1999, A Novel Twist on Binge Eating Treatment, Psychiatric Dispatches in Primary Psychiatry; 6(10):24-29.

Paile-Hyvarinen et al., Mar. 14, 2003, Quality of life and metabolic status in mildly depressed women with type 2 diabetes treated with paroxetine: a single blind randomised placebo controlled trial, BMC Family Practive, Biomed Central, 4(1), 6 pp.

Paar et al., 2002, Bivalent ligands with rigid double-stranded DNA spacers reveal structural constraints on signaling by FceRI, J. Immunol., 169:856-864.

Pasternak et al. (1980) Long-acting opiate agonists and antagonists: 14-hydroxydihydromorphinone hydrazones, Med. Chem, 23:674-676.

Pavuluri et al. (2002) Topiramate Plus Risperidone for Controlling Weight Gain and Symptoms in Preschool Mania, Journal of Child and Adolescent Psychopharmacology, 12(3):271-273.

Penn et al., 2003, Pharmacotherapy of obesity in the near term, Current Opinion in Endocrinology and Diabetes, 18(2):311-316.

Portoghese et al., 1982, Opioid agonist and antagoinst bivalent ligands as receptor probes, Life Sciences, 31:1283-1286.

Portoghese et al., 1986, Synthesis and Opioid antagonit potencies of naltrexamine bivalent ligands with conformationally restricted spacers J. Med. Chem., 29:1650-1653.

Portoghese et al., 1986, Opioid agonist and antagonist bivalent ligands. The relationship between spacer length and selectivity at multiple opioid receptors, J. Med. Chem., 29:1855-1861.

Portoghese, 1992, The role of concepts in structure-activity relationship studies of opioid ligands, J. Med. Chem., 35:1927-1937.

Potter et al., 1997, Sustained Weight Loss Associated with 12-month topiramate Therapy, Epilepsia, Raven Press Ltd. New York, 38(Suppl 8):97.

Rao et al. (1998) Fixed-does combination therapy: panacea or poison?, Intensive Care Med, 24:283-285.

Reaven, G. M. 1995. Pathophysiology of insulin resistance in human disease. Physiological Reviews, 75(3):473-486.

Reents et al. (1988) Nalozone and naltrexone, Chest, 93(1):217-219.

Remington's Pharmaceutical Sciences. $18^{th}$ Edition; Easton, PA: Mack Publishing Co. (1990).

Reneric et al. (Nov. 1998) Opioid Receptor Antagonists in Psychiatry, CNS Drugs, 10(5):365-377.

Rezvani et al. 2000. Combination pharmacotherapy: A mixture of small doses of naltrexone, fluoxetine, and thyrotropin-releasing hormone analogue reduces alcohol intake in three strains of alcohol-preferring rats. Alcohol & Alcoholism, 35(1):76-83.

Romano et al. 2001. Long-term treatment of obsessive-compulsive disorder after an acute response: A comparison of fluoxetine versus placebo. Journal of Clinical Psychopharmacology, 21(1):46-52.

Rotzinger et al. (1999) Metabolism of some 'second' and 'fourth' generation antidepressants: iprindole, viloxazine, bupropin, mianserin, maprotiline, trazadone, nefazodone, and vaniafaxine, Cellular and Molecular Neurobiology, 19:430.

Rowland et al. (2001) Effects of the cannabinoid receptor antagonist SR 141716, alone and in combination with dexfenfluramine or naloxone, on food intake in rats. Psychopharmacology; 159:111-116.

Saba et al. 2002. Lamotrigine-clozapine combination in refractory schizophrenia: Three cases. The Journal of Neuropsychiatry and Clinical Neurosciences, 14(1):86.

Sackellares et al. (1985) Pilot study of zonisamide (1,2-benzisoxazole-3-methanesulfonamide) in patients with refractory partial seizures. Epilepsia, 26(3):206-211.

Saper et al. (2002) The need to feed: Homeostatic and hedonic control of eating, Neuron, 36:199-211.

Sashiwa et al., 2000, Chemical modification of chitosan. 3. Hyperbranched chitosan-sialic acid dendrimer hybrid with tetraethylene glycol spacer, Macromolecules, 33:6913-6915.

Sayre et al., 1984, Design and synthesis of naltrexone-derived affinity labels with nonequilibrium opioid agonist and antagonist activities. Evidence for the existence of different receptor subtypes in different tissues, J. Med. Chem., 27:1325-1335.

Scheen et al., May 1, 2005, Diabete sucre iatrogene: l'exemple des anti-phsychogiques atypiques, Revue Medicale de Liege, 60(5-6):455-460.

Schmidhammer et al. (1994) Mixed Azines of Naloxone with Dihydromorphinone Derivatives. A. Helv. Chim. Acta; 77:999.

Schmidt et al. (1993) Zonisamide for add-on treatment of refractory partial epilepsy: a European double-blind trial. Epilepsy Research; 15:67-73.

Schimmel et al., 1974, Inhibition by diphenylhydantoin of the diabetogenic actioon of streptozocin, Horm. Metab. Res. 6:475-477.

Shapira et al. (2000) Treatment of Binge-Eating Disorder with Topiramate: A Clinical Case Series. J. Clin. Psychiatry; 61(5):368-371.

Shapira et al. 2004. A double-blind, placebo-controlled trial of olanzapine addition in fluoxetine-refractory obsessive-compulsive disorder. Biol. Psychiatry, 550:553-555.

Shapiro et al. (2005) Additive Benefits of Combination Therapy with Sibutramine and Rimonabant on Body Weight, Insulin Sensitivity and Lipoproteins in Diet-Induced Obese Mice, 2005 NAASO Annual Meeting, Poster 405-P.

Shelton (2003) Classification of Antidepressants and their Clinical Implications, Primary Care Companion J. Clin. Psychiatry, 5(Supp. 7):27-32.

Shriqui et al. (Jul. 2002) Atypical Antipsychotics, The Canadian Journal of CME, pp. 65-80.

Sitsen et al., 2001, Drug-drug interaction studies with mirtazapine and carbamazepine in healthy male subjects, European Journal of Drug Metabolism and Pharmacokinetics, 26(1-2):109-121.

Sneer et al., Protective effect of diphenylhydantoin on the diabetes-inducing effect of alioxan, database accession No. 1980:34024.

Spigset et al. (2001) Therapeutic Approaches to Bulimia Nervosa, Expert Opinion on Therapeutic Patents, 11(3):463-477.

Srivastava et al. 1975. Organic disulfides and related substances. 38. Some disulfide and trisulfide sulfinate salts as antiradiation drugs. Journal of Medicinal Chemistry, 18(8):798-802.

Steffen et al. 2006. Emerging drugs for eating disorder treatment. Expert Opin. Emerging Drugs, 11(2):315-336.

Stein (Feb. 15, 2000) Neurobiology of the obsessive-compulsive spectrum disorders, Biological Psychiatry 47(4):296-304.

Stein (Aug. 3, 2002) Obsessive-compulsive disorder, Lancet 360(9330):397-405.

Stepinski et al. (1991) Internat. J. of Peptide & Protein Res., 38:588-592.

Storch et al. 2006. Clinical predictors of early fluoxetine treatment response in obsessive-compulsive disorder. Depression and Anxiety, 23:429-433.

Stromberg et al. (2002) A comparison of the effects of 6-beta naltrexol and naltrexone on the consumption of ehanol or sucrose using a limited-access procedure in rats. Pharmacology, Biochemistry, and Behavior, 72:483-490.

Swedo et al. 1998. Pediatric autoimmune neuropsychiatric disorders associated with streptococcal infections: Clinical description of the first 50 cases. Am. J. Psychiatry, 155(2):264-271.

Symons et al. 2004. Self-injurious behavior and the efficacy of naltrexone treatment: A quantitative synthesis. Mental Retardation and Developmental Disabilities Research Reviews, 10:193-200.

Tamiz et al., 2000, Application of the bivalent ligand approach to the design of novel dimeric serotonin reuptake inhibitors, J. Am. Chem. Soc., 122:5393-5394.

Tamiz et al., 2001, Pharmacological and behavioral analysis of the effects of some bivalent ligand-based monoamine reuptake inhibitors, J. Med. Chem., 44:1615-1622.

Testa, 2004, Prodrug research: futile or fertile?, Biochemcial Pharmacology, 68:2097-2106.

Thearle et al. (2003) Obesity and Pharmacology, Endocrinology and Metabolism Clinics of North American, W.B. Suanders Company, Philadelphia US 32(4):1005-1024.

Thombre et al. (2004) Osmotic drug delivery using swellable-core technolgoy, Journal of Controlled Release 94:75-89.

Tollefson et al. (1997) Olanzine versus haloperidol in the treatment of schizophrenia and schizoaffective and schizophreniform disorders: results of an international collaborative trial, Am J. Psychiatry, 154(5):457-465.

Tutka et al., 2004, Convulsant and anticonvulsant effects of bupropion in mice, European Journal of Pharmacology, 499:117-120.

Van Schaftingen et al. (1992) The regulatory protein of liver glucokinase. Advan. Enzyme Regul., 32:133-148.

Vieta et al. (2003) 1-year follow-up of patients treated with risperidone and topiramate for a manic episode, J Clin Psychiatry, 64(7):834-829.

Vieta et al. (2004) Effects on weight and outcome of long-term olanzapine-topiramate combination treatment in bipolar disorder. Journal of Clinical Psychopharmacology 24(4):374-378.

Vythilingum et al. 2005. Obsessive-compulsive disorders and dermatologic disease. Dermatologic Clinics, 23:675-680.

Wadden et al. (2000) Effects of Sibutramine Plus Orlistat in Obese Women Following 1 Year of Treatment by Sibutramine Alone: A Placebo-Controlled Trial, Obesity Research; 8(6):431.

Walker et al. (1988) Chronic Toxicity of the Anticonvulsant Zonisamide in Beagle Dogs, Fundamental and Applied Toxicology 11:333-342.

Wang et al. (2002) Gabapentin augmentation therapy in bipolar depression, Bipolar Disorders 4:296-301.

Weintraub et al. (1992) Long-term Weight Control Study I (weeks 0 to 34) 'The Enhancement of Behavior Modification, Caloric Restriction, and Exercise by Fenfluramine Plus Phentermine versus Placebo', Clinical Pharmacology & Therapeutics, 51(5):586-94.

Welty et al. (Nov. 30-Dec. 5, 2001) Weight Loss Associated With Use of Zonisamide in European and US Clinical Trials, A Compendium of Posters and Platform Sessions for Zonegran®, Presented at the Annual Meeting 2001 of the American Epilepsy Society, Philadelphia, Pennsylvania.

Wermuth, Apr. 2006, Similarity in drugs: reflectionson analyogue design, Drug Discovery Today, 11(7/8):348-354.

Werneke et al. (2002) Options for Pharmacological Management of Obesity in patients Treated with Atypical Antipsychotics, International Clinical Psychopharmacology, 17(4):145-160.

Wheatley et al., 1998, Mirtazapine: efficacy and tolerability in comparison with fluoxetine in patients with moderate to severe major depressive disorder, J. Clin Psychiatry, 59(6):306-312, Abstract.

White et al. 2002. Development and validation of the food-craving inventory. Obesity Research, 10(2):107-114.

Wilding (2004) Clinical evaluation of anti-obesity drugs. Current Drug Targets; 5:325-332.

Willmore, L. J. 2004. Commentary on Leppik. Seizure, 13S:S10.

Wilner, 2002, Is Weight Loss With Zonisamide Gender-Specific?, Annual Meeting of the American Epilepsy Society, https://secure.neurohub.net/cgi-perl/get.cgi?pub=52318&ext=htm, 1 pp.

Wolff, 1995) Burger's Medicial Chemsitry and Drug Discovery, John Wiley & Sons, 5th Ed. 1:975-977.

Yeomans et al. (2002) Opioid peptides and the control of human ingestive behaviour, Neuroscience and Biobehavioral Reviews, 26:712-728.

Yoshimasu et al. (2003) Psychotropic Drug-Induced Obesity, Nippon Rinsho, 61(Suppl. 6):825-829. (English translation of Japanese Office Action containing Examiner's characterization of reference is appended to reference: Notice of Reasons for Rejection, Application No. 2006-549530).

Yu et al. (2005) Influence of insulin treatment on isnulin sensitivity in insula requiring type 2 diabetes patents, Diabetes Research and Clinical Practice, 68S1:S54-S59.

Zeng et al., 1988, Convenient synthesis of 9-alkyl and 9-arylacridines from [2-(trimethylsilyl)ethoxy]methyl (sem) protected acridone, Tetrahedron Letters, 29(40):5123-5124.

Zhang et al. (1994) Positional Cloning of the Mouse obese gen and its humane homologue, Nature, 372:425-432.

Zhu et al. (Apr. 3, 2002) Pharmacologic Treatment of Easting Disorders, Canadian Journal of Psychiatry, 47(3):227-234.

Zitterl et al. 1999. Efficacy of fluoxetine in Austrian patients with obsessive-compulsive disorder. Wiener Klinische Wochenschrift, 111(11):439-442.

Zohar et al. 1987. Serotonergic responsivity in obsessive-compulsive disorder. Arch. Gen. Psychiatry, 44:946-951.

Zonegran.TM. (zonisamide) capsules, FDA Approved Labeling Text, Mar. 27, 2000, 24 pp.

Zonisamide (Oral Route), MayoClinic.com, 12 pp., 2009.

IPRP for PCT/US07/084177, dated May 22, 2009.

* cited by examiner

LAYERED PHARMACEUTICAL FORMULATIONS

The present application claims priority from U.S. Provisional Patent Application Ser. No. 60/865,157, filed Nov. 9, 2006, which is hereby incorporated by reference in its entirety.

BACKGROUND

1. Field of the Invention

This invention relates to pharmaceutical formulations having two or more pharmaceutical layers interspersed with one or more intermediate layers, wherein the pharmaceutical layers include, but are not limited to, pharmaceutical compositions useful for affecting weight loss, suppressing appetite and/or treating obesity-related conditions in individuals.

2. Description of the Related Art

Certain types of layered tablets are known in pharmaceutical applications. Some pharmaceutical applications separate potentially interacting layers from one another within a tablet. For example, U.S. Pat. No. 6,576,256 discloses separating potentially interacting compounds from each other using separate flat layers of a tablet, concentric layers, coated beads or granules, and/or using buffers. Thombre, A. G., L. E. Appel, et al. (2004), "Osmotic drug delivery using swellable-core technology" J. Control Release 94(1): 75-89 discloses a core tablet containing a drug and a water-swellable component, and one or more delivery ports in different core configurations including a tablet-in-tablet (TNT) bilayer and trilayer formation. U.S. Pat. No. 6,706,283 discloses an osmotic delivery device fabricated in a bilayer geometry, wherein the core comprises a sweller layer "sandwiched" between two drug layers. The coating of a bilayer tablet may include a water permeable membrane, but is substantially impermeable to the drug and/or the excipients contained therein. U.S. Pat. No. 6,630,165 discloses dosage forms and methods for providing sustained release reboxetine including a trilayered compressed core with a first component drug layer, a second component push layer and a third component barrier layer separating the drug layer from the push layer. The barrier layer is inert with the respect to the composition of the drug layer and substantially impermeable, such that the drug and the components of the push layer are prevented from mixing.

Among multiple layer tablet forms, one type includes a first layer to provide immediate release of a drug and a second layer to provide controlled-release of the drug. U.S. Pat. No. 6,514,531 discloses coated trilayer immediate/prolonged release tablets comprising zolpidem hemitartrate. U.S. Pat. No. 6,087,386 discloses a trilayer tablet with an enalapril layer, a losartan potassium layer and a second enalapril maleate layer or an excipient layer. U.S. Pat. No. 5,213,807 discloses an oral trilayer tablet with a core comprising a nonsteroidal anti-inflammatory drug (NSAID), ibuprofen and ibuprofen salts and an intermediate coating comprising a substantially impervious/impermeable material to the passage of ibuprofen. U.S. Pat. No. 6,926,907 discloses a trilayer tablet that separates famotidine contained in a film coat from a core comprising controlled-release naproxen formulated using excipients which control the drug release. The film coat is an enteric coating configured to delay the release of naproxen until the dosage form reaches an environment where the pH is above four.

SUMMARY

An embodiment provides a layered pharmaceutical formulation comprising two or more pharmaceutical layers and an intermediate layer disposed between at least two of the two or more pharmaceutical layers. In some embodiments the intermediate layer is configured to dissolve in vivo to thereby leave the two or more pharmaceutical layers substantially intact, but physically separated, essentially forming two distinct pills. In some embodiments the dissolution rate of one of the separated two or more pharmaceutical layers is substantially similar to that of a singly compressed tablet comprising the same pharmaceutical composition as that of the pharmaceutical layer.

Use of a first compound and a second compound in the preparation of a medicament for affecting weight loss, suppressing appetite and/or treating an obesity-related condition, wherein the medicament comprises layered pharmaceutical formulations of the present invention.

BRIEF DESCRIPTION OF THE DRAWINGS

Other aspects of the disclosure will be readily apparent from the description below and the appended drawings, in which like reference numerals refer to similar parts throughout, which are meant to illustrate and not to limit the disclosure, and in which.

DETAILED DESCRIPTION OF THE PREFERRED EMBODIMENT

Figure 1A:
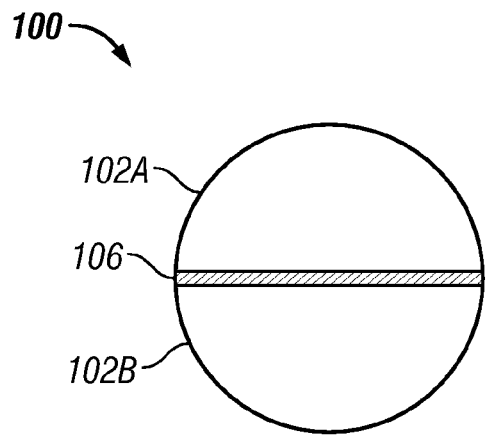
FIG. 1A illustrates an embodiment of a layered pharmaceutical formulation.

Embodiments of the present disclosure provide significant improvements to multilayer tablet technology. In an embodiment, a layered pharmaceutical formulation comprises two or more pharmaceutical layers and at least one intermediate layer disposed between at least two of the two or more pharmaceutical layers. The at least one intermediate layer is configured to dissolve in vivo to thereby leave the two or more pharmaceutical layers substantially intact. In some embodiments the dissolution rate of one or more of a separated pharmaceutical layer is substantially similar to that of a singly compressed tablet comprising the same pharmaceutical composition as that of the pharmaceutical layer. The separated pharmaceutical layer thus has an independent and predictable dissolution profile.

A dissolution profile for a drug comprises the known dissolution rate and particular dissolution characteristics of the drug. A predictable dissolution profile for a specific drug allows for more accurate treatment of a given symptom. Predictable dissolution profiles for different drugs within a multilayer tablet allow for coordinated treatment of multiple symptoms with a single pharmaceutical formulation.

In general, multilayer pharmaceutical formulations present challenges in maintaining predictable dissolution profiles. For example, in vivo conditions often disrupt an otherwise predictable multilayer pharmaceutical formulation dissolution profile. A multilayer tablet may be manufactured with drugs of known dissolution profiles. Once the multilayer tablet is ingested by a patient, however, there is no guarantee that each drug will dissolve as predicted by its individual dissolution profile. Drug configuration within a tablet, tablet shape, excipients or fillers in the tablet, tablet coatings and in vivo conditions may all affect the dissolution profiles. Additionally, interaction between different drugs within a multilayer tablet may cause a change in dissolution profile for one or more compositions within the multilayer tablet.

Further, in one possible in vivo condition, if the multilayer tablet becomes attached to the lining of the stomach, only a portion of the tablet would be exposed to the stomach fluids. The dissolution of the exposed portion of the tablet may occur at a more predictable rate while the unexposed portion of the multilayer tablet shielded from the stomach fluids would have a longer dissolution profile than would otherwise be expected from a singly compressed tablet of an identical composition. As mentioned above, having a multilayer tablet is desirable for ease of administration of multiple pharmaceutical compositions within a single tablet. Thus, it is desirable to configure a multilayer pharmaceutical formulation such that each pharmaceutical layer has a predictable dissolution profile.

Herein disclosed is a pharmaceutical formulation comprising two or more pharmaceutical layers and at least one intermediate layer configured to dissolve in vivo to thereby leave the two or more pharmaceutical layers substantially intact. In preferred embodiments the dissolution rate of one or more of the separated pharmaceutical layers is substantially similar to that of a singly compressed tablet comprising the same pharmaceutical composition as that of the pharmaceutical layer. In some embodiments, the pharmaceutical layer comprises a single pharmaceutically active compound or drug. In other embodiments the pharmaceutical layer comprises a pharmaceutical composition. The term "pharmaceutical composition" refers to a mixture of a chemical compound or compounds (e.g., a drug or drugs) with additional pharmaceutical components, such as diluents or carriers. Herein, the term "drug" is synonymous with the term "pharmaceutically active ingredient." The pharmaceutical composition facilitates administration of the drug to an organism. Pharmaceutical compositions can also be obtained in the form of pharmaceutically acceptable salts by reacting drug compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

In some embodiments the two or more pharmaceutical layers comprise one or more immediate-release formulations. The term "immediate-release" is used herein to specify that the immediate release formulation is not configured to alter the dissolution profile of the pharmaceutical layer. For example, an immediate release pharmaceutical layer may be a pharmaceutical composition that does not contain ingredients included for the purpose of altering the dissolution profile. In some embodiments the two or more pharmaceutical layers comprise one or more controlled-release formulations. The term "controlled-release" is used herein in its ordinary sense and thus includes pharmaceutical compositions combined with ingredients to alter their dissolution profile. A "sustained-release" formulation is a type of controlled-release formulation, wherein ingredients have been added to a pharmaceutical composition such that the dissolution profile is extended over a longer period of time than that of an immediate release formulation comprising a similar pharmaceutical composition.

In some embodiments the at least one intermediate layer is a flat layer separating at least two pharmaceutical layers. In some embodiments the at least one intermediate layer has exposed edges. Exposed edges allow for fluid to contact and dissolve the at least one intermediate layer. In some embodiments the pharmaceutical formulations comprises a coating covering the two or more pharmaceutical layers and the at least one intermediate layer. The coating is configured to dissolve in vivo more or less uniformly over the two or more pharmaceutical layers and the at least one intermediate layer such that the at least one intermediate layer is left exposed to the fluids that will dissolve the at least one intermediate layer in vivo.

In some embodiments the at least one intermediate layer is or comprises an impermeable membrane. In some embodiments the at least one intermediate layer has a substantially higher dissolution rate than at least one of the pharmaceutical layers. In some preferred embodiments the at least one intermediate layer dissolves in a nearly immediate fashion with respect to the dissolution of at least one of the pharmaceutical layers. In some embodiments the at least one intermediate layer comprises at least one of a monosaccharide or a disaccharide sugar, a starch (e.g., corn or potato starches), or any other suitable tablet ingredients known in the art. In some preferred embodiments the at least one intermediate layer comprises lactose. In some preferred embodiments, the intermediate layer dissolves in a nearly immediate fashion as compared to the dissolution rates of the respective pharmaceutical layers, e.g., such that upon dissolution of the intermediate layer, substantially all of the surface area of each of the two pharmaceutical layers is exposed. Thus, in one embodiment, under a standard dissolution test the immediate release layer is dissolved to the extent that at least two pharmaceutical layers present in the pharmaceutical formulation are separated in less than 0.1, 0.2, 0.3, 0.4, 0.5, 0.6, 0.7, 0.8, 0.9, 1, 2, 3, 4, 5, 6, 7, 8, 9, 10, 15, 20, 25 or 30 minutes.

Pharmaceutical formulations of drugs can be configured in various ways and in a variety of dosage forms to modify a dissolution rate of the drug. For example, one type of controlled-release pharmaceutical formulation is a sustained-release pharmaceutical formulation. Sustained-release pharmaceutical formulations can contain a variety of excipients, such as retardant excipients (also referred to as release modifiers) and/or fillers that are selected and incorporated into the formulation in such a way as to slow the dissolution rate of the formulation (and thereby slow the dissolution and/or release of the zonisamide) under in vivo conditions as compared to an otherwise comparable immediate-release formulation. Thus, a "comparable" immediate-release formulation is one that is substantially identical to the controlled-release formulation, except that that it is configured to provide immediate-release instead of controlled-release under substantially identical conditions.

The term "immediate-release" is used herein to specify a formulation that is not configured to alter the dissolution profile of the active ingredient (e.g., zonisamide, bupropion, naltrexone, olanzapine, phentermine, topiramate, metformin, fluoxetine). For example, an immediate-release pharmaceutical formulation may be a pharmaceutical formulation that does not contain ingredients that have been included for the purpose of altering the dissolution profile. An immediate-release formulation thus includes drug formulations that take less than 30 minutes for substantially complete dissolution of the drug in a standard dissolution test. A "standard dissolution test," as that term is used herein, is a test conducted according to United States Pharmacopeia 24th edition (2000) (USP 24), pp. 1941-1943, using Apparatus 2 described therein at a spindle rotation speed of 100 rpm and a dissolution medium of water, at 37° C., or other test conditions substantially equivalent thereto. The term "controlled-release" is used herein in its ordinary sense and thus includes pharmaceutical formulations that are combined with ingredients to alter their dissolution profile. A "sustained-release" formulation is a type of controlled-release formulation, wherein ingredients have been added to a pharmaceutical formulation such that the dissolution profile of the active ingredient is extended over a longer period of time than that of an otherwise comparable immediate-release formulation. A controlled-release formulation thus includes drug formulations that take 30 minutes or longer for substantially complete dissolution of the drug in a standard dissolution test, conditions which are representative of the in vivo release profile.

A pharmaceutical layer may be configured in various ways. For example, in some embodiments a layer comprises a flat portion of a pharmaceutical formulation. In some embodiments a layer comprises a rounded portion of a pharmaceutical formulation. In some embodiments a layer comprises a conical section of a pharmaceutical formulation. In some embodiments a layer comprises an elliptical section of a pharmaceutical formulation. In some embodiments a layer comprises a sideways section of a pharmaceutical formulation. In some embodiments a layer comprises a cubical section of a pharmaceutical formulation. In some embodiments a layer comprises a wedge of a pharmaceutical formulation. In some embodiments a layer comprises a substantial portion of a pharmaceutical formulation. A substantial portion is preferably at least about 25% of the pharmaceutical formulation and more preferably at least about 50% of the pharmaceutical formulation.

In some embodiments at least one pharmaceutical layer reacts when brought into contact with another of the pharmaceutical layers within the layered pharmaceutical formulation. In some embodiments at least one pharmaceutical layer does not react when brought into contact with another of the pharmaceutical layers.

In some embodiments an intermediate layer is configured to dissolve in vivo. Dissolving is the act of solvation wherein a solute is dissolved in a solvent to create a solution. Dissolving in vivo means that the dissolving takes place within an organism or within living tissue either taken from or part of an organism. An organism is any living animal, plant, bacteria or fungus. In preferred embodiments the organism is human.

In some embodiments a dissolving intermediate layer separates at least two of the pharmaceutical layers. In some embodiments the two pharmaceutical layers contain different pharmaceutical compositions. In some embodiments after the intermediate layer dissolves, the pharmaceutical layers are no longer held together within the pharmaceutical formulation. In some embodiments after the intermediate layer dissolves, the pharmaceutical layers remain substantially intact. A pharmaceutical layer remains substantially intact when it retains at least about 50% of its original mass in a single entity post-dissolution of the one or more intermediate layers. In preferred embodiments the pharmaceutical layer remains substantially intact when it retains at least about 75% of its original mass post-dissolution of the one or more intermediate layers. In more preferred embodiments the pharmaceutical layer remains substantially intact when it retains at least about 85% of its original mass post-dissolution of the one or more intermediate layers. In some embodiments each pharmaceutical layer has a different dissolution rate. A dissolution rate is the salvation of a pharmaceutical layer volume per unit time. In some embodiments one or more pharmaceutical layers have similar dissolution rates. Preferably the one or more intermediate layers have a higher dissolution rate than the two or more pharmaceutical layers.

FIG. 1A illustrates a preferred embodiment of a pharmaceutical formulation 100. The pharmaceutical formulation 100 comprises two pharmaceutical layers 102A and 102B. Pharmaceutical layer 102A comprises a pharmaceutical composition. In some embodiments of the pharmaceutical formulation 100, the pharmaceutical layer 102B comprises the same pharmaceutical composition as that of the pharmaceutical layer 102A. In the illustrated embodiment of pharmaceutical formulation 100, the pharmaceutical layer 102A comprises a different pharmaceutical composition than that of the pharmaceutical layer 102B. The pharmaceutical formulation 100 also comprises an intermediate layer 106. In the illustrated embodiment the intermediate layer 106 is configured to dissolve in vivo.

Each of the pharmaceutical layers 102A and 102B comprises one or more pharmaceutical compositions. As illustrated in the pharmaceutical formulation 100, the dosage amount of each pharmaceutical layer 102A and 102B is similar. The dosage strength of each pharmaceutical layer may also be similar. In other embodiments the dosage amount and/or strength of one pharmaceutical layer is much greater than that of another layer. This difference in dosage amount or strength allows for individualized treatment of symptoms that are addressed by increasing or decreasing a dosage of one or more pharmaceutical layers while maintaining a dosage of other layers. The amount or strength of dosage of a drug contained within a pharmaceutical formulation will, of course, be dependent on the subject being treated, on the subject's weight, the severity of the affliction, the manner of administration and the judgment of the prescribing physician.

The illustrated pharmaceutical formulation 100 includes, but is not limited to, drugs for affecting weight loss, suppressing appetite and/or treating an obesity-related condition in a patient. Specifically, the illustrated pharmaceutical layer 102A comprises zonisamide and the pharmaceutical layer 102B comprises bupropion. The intermediate layer 106 comprises lactose or a suitable monosaccharide sugar, disaccharide sugar or a starch. In another embodiment, one or more of the pharmaceutical layers comprises naltrexone, one or more of the pharmaceutical layers comprises bupropion, and at least one intermediate layer comprises a monosaccharide sugar, a disaccharide sugar or a starch. In another embodiment, one or more of the pharmaceutical layers comprises naltrexone, one or more of the pharmaceutical layers comprises zonisamide, and at least one intermediate layer comprises a monosaccharide sugar, a disaccharide sugar or a starch. In another embodiment, one or more of the pharmaceutical layers comprises naltrexone, one or more of the pharmaceutical layers comprises fluoxetine, and at least one intermediate layer comprises a monosaccharide sugar, a disaccharide sugar or a starch. In another embodiment, one or more of the pharmaceutical layers comprises olanzapine, one or more of the pharmaceutical layers comprises zonisamide, and at least one intermediate layer comprises a monosaccharide sugar, a disaccharide sugar or a starch. In another embodiment, one or more of the pharmaceutical layers comprises metformin, one or more of the pharmaceutical layers comprises zonisamide, and at least one intermediate layer comprises a monosaccharide sugar, a disaccharide sugar or a starch. In another embodiment, one or more of the pharmaceutical layers comprises phentermine, one or more of the pharmaceutical layers comprises topiramate, and at least one intermediate layer comprises a monosaccharide sugar, a disaccharide sugar or a starch.

In some embodiments the presence of one drug in a pharmaceutical formulation enhances the desired physiological effects and/or reduces undesired physiological effects of one or more other drugs in the pharmaceutical formulation. In some embodiments the presence of one or more drugs in a pharmaceutical formulation enhances the desired physiological effects of the drugs over the additive physiological effects of the one or more drugs in comparable, but separate pharmaceutical formulations when administered alone.

Figure 1B:
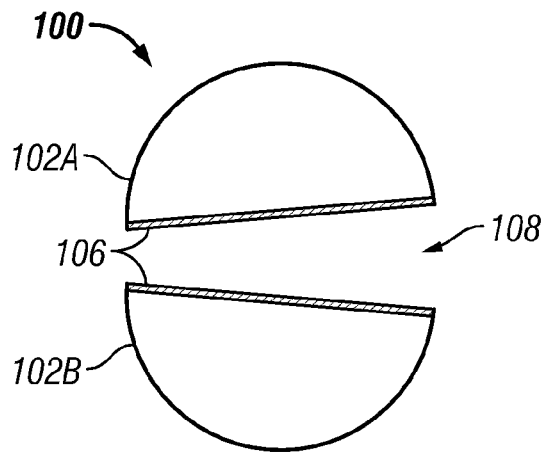
FIGS. 1B & 1C illustrate the layered pharmaceutical formulation of FIG. 1A in progressive stages as an intermediate layer dissolves.

FIG. 1B illustrates the pharmaceutical formulation 100 of FIG. 1A as a fluid, as represented by the arrow 108, begins to dissolve the intermediate layer 106. In the illustrated embodiment, the fluid comprises at least one bodily fluid selected from saliva, sweat, chyme, mucus and bile. As the intermediate layer 106 dissolves the pharmaceutical layers 102A and 102B begin to separate as shown. As noted above, in some embodiments each pharmaceutical layer comprises the same pharmaceutical composition. However, in the illustrated embodiment, the pharmaceutical layers 102A and 102B each comprise a different pharmaceutical composition. In some embodiments, one or more of the pharmaceutical layers comprises a controlled-release formulation. In some embodiments, one or more of the controlled-release formulations comprises a sustained-release formulation.

Figure 1C:
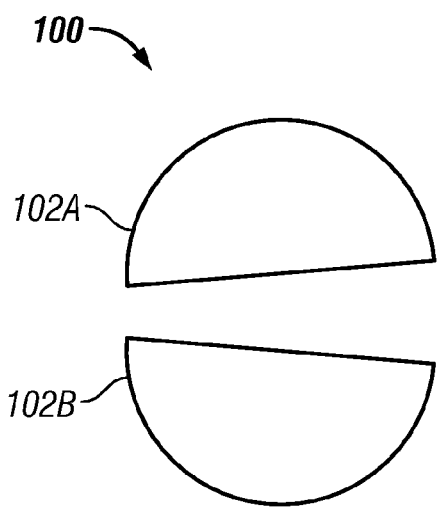

FIG. 1C illustrates the layered pharmaceutical formulation 100 of FIG. 1A after the intermediate layer 106 has completely dissolved. The pharmaceutical layers 102A and 102B have separated and remain substantially intact.

Figure 2A:
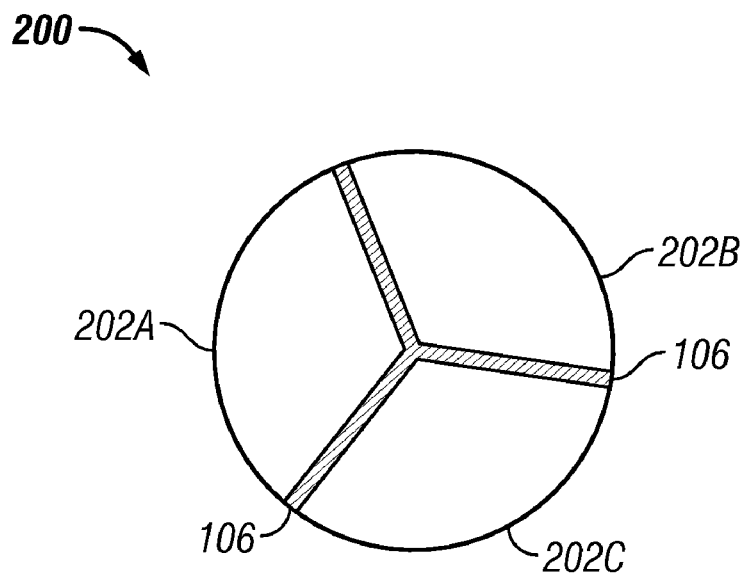
FIG. 2A illustrates a second embodiment of a layered pharmaceutical formulation.

FIG. 2A illustrates an embodiment of a second layered pharmaceutical formulation 200. The second pharmaceutical formulation 200 comprises second pharmaceutical layers 202A, 202B and 202C. In some embodiments two or more of the second pharmaceutical layers 202A, 202B and 202C comprise the same pharmaceutical composition. In the illustrated embodiment each of the pharmaceutical layers 202A, 202B and 202C comprises a different pharmaceutical composition. The second pharmaceutical formulation 200 also comprises an intermediate layer 106 configured to dissolve in vivo.

Figure 2B:
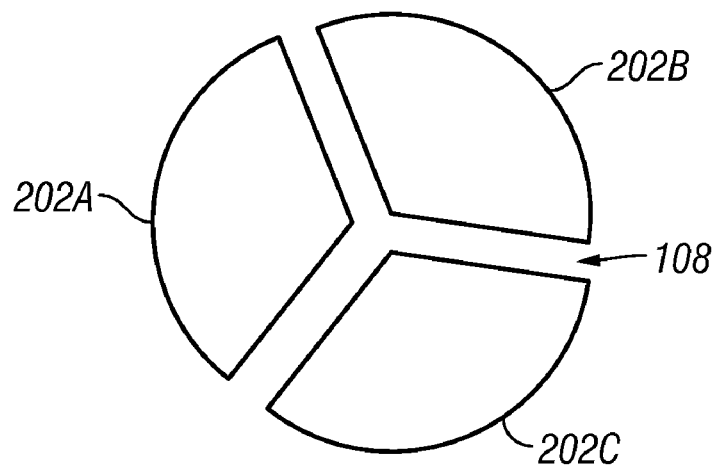
FIG. 2B illustrates the second embodiment of FIG. 2A after an intermediate layer dissolves.

FIG. 2B illustrates the second layered pharmaceutical formulation 200 of FIG. 2A. The fluid, as represented by the arrow 108, has dissolved an intermediate layer 106 and the second pharmaceutical layers 202A, 202B and 202C are separated and left substantially intact.

Figure 3:
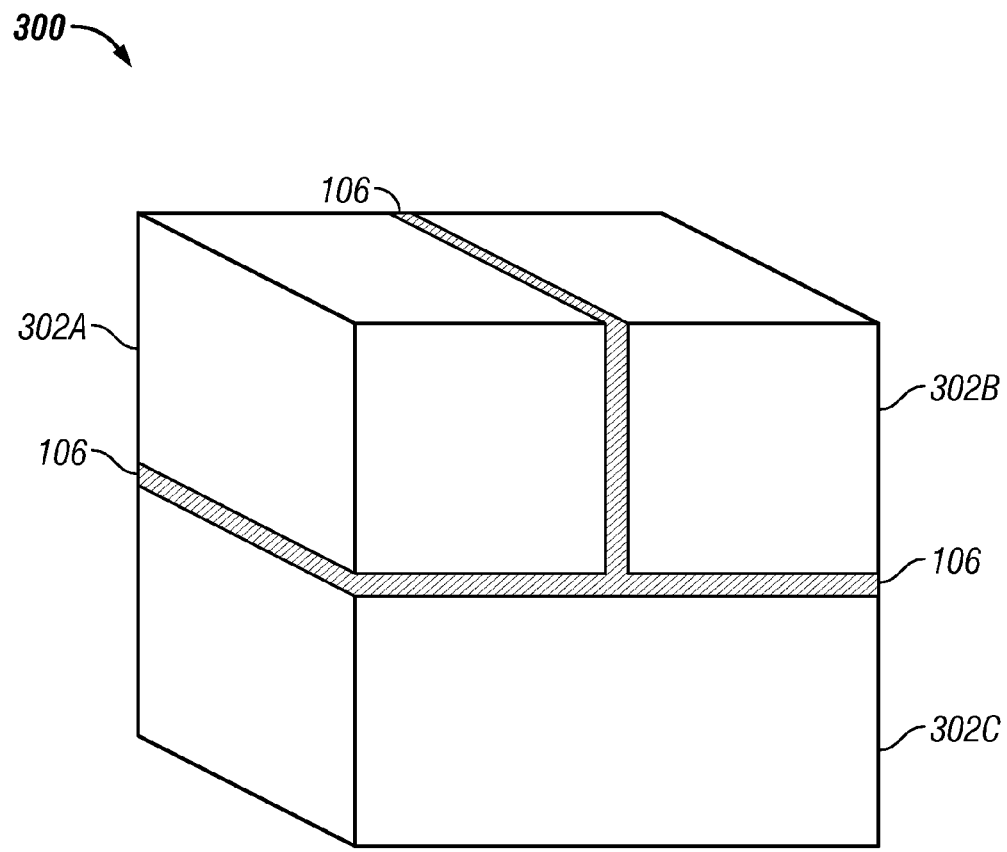
FIG. 3 illustrates a third embodiment of a layered pharmaceutical formulation.

FIG. 3 illustrates an embodiment of a third layered pharmaceutical formulation 300. The third pharmaceutical formulation 300 comprises third pharmaceutical layers 302A, 302B and 302C separated by an intermediate layer 106. Each of the third pharmaceutical layers 302A, 302B and 302C comprises one or more pharmaceutical compositions. As illustrated in the third layered pharmaceutical formulation 300, the third pharmaceutical layer 302A comprises a similar dosage volume to the third pharmaceutical layer 302B. The third pharmaceutical layer 302C, however, comprises a larger dosage volume than third pharmaceutical layers 302A or 302B. As noted above with regard to FIG. 1, varying dosage amounts or strengths of particular pharmaceutical layers within a pharmaceutical formulation allows for individualized treatment of particular symptoms.

Figure 4:
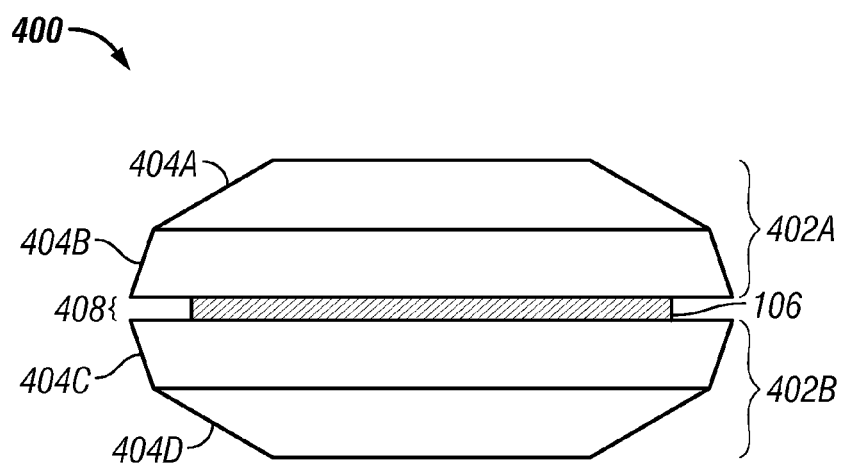
FIG. 4 illustrates a fourth embodiment of a layered pharmaceutical formulation.

FIG. 4 illustrates an embodiment of a fourth layered pharmaceutical formulation 400. The fourth pharmaceutical formulation 400 includes, but is not limited to fourth pharmaceutical layers 402A and 402B and an intermediate layer 106. The fourth pharmaceutical layer 402A comprises a first drug 404A and a second drug 404B. The first drug 404A and the second drug 404B are positioned within the fourth pharmaceutical layer 402A so as to be in physical contact with the other; no intermediate layer 106 separates the first drug 404A from the second drug 404B within the layer 402A. Similarly, the fourth pharmaceutical layer 402B comprises a third drug 404C and a fourth drug 404D; no intermediate layer 106 separates the third drug 404C and the fourth drug 404D.

In the fourth pharmaceutical formulation 400 the intermediate layer 106 is disposed between fourth pharmaceutical layers 402C and 402B. In this embodiment, the edges of intermediate layer 106 are not aligned with the fourth pharmaceutical layers 402C and 402B. A space 408 allows for fluids to interact with and dissolve the intermediate layer 106. Thus, although the intermediate layer 106 is not flush with the outside edge of the fourth pharmaceutical formulation 400, the intermediate layer 106 is exposed for purposes of dissolution upon contact with bodily fluids.

Figure 5:
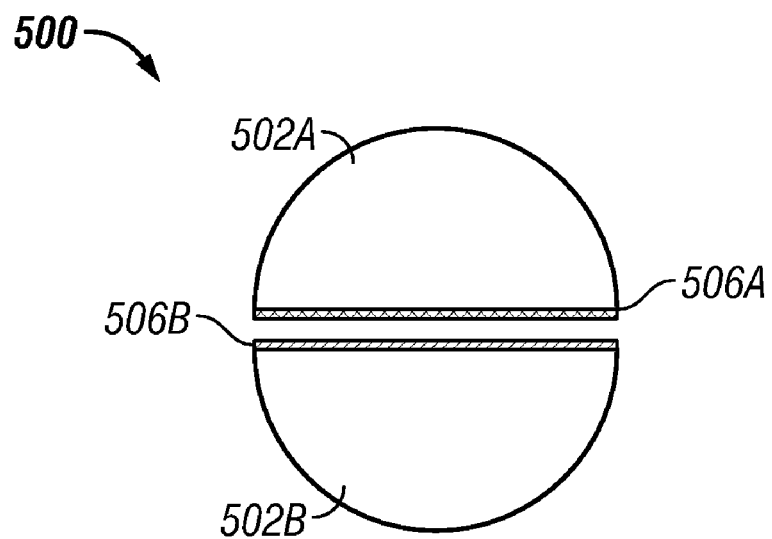
FIG. 5 illustrates a fifth embodiment of a layered pharmaceutical formulation with multiple intermediate layers.

FIG. 5 illustrates an embodiment of a fifth layered pharmaceutical formulation 500 depicted after separation has occurred. The fifth pharmaceutical formulation 500 includes, but is not limited to fifth pharmaceutical layers 502A and 502B. The fifth pharmaceutical layers 502A and 502B each include, but are not limited to one or more pharmaceutical compositions.

The fifth pharmaceutical formulation 500 further comprises a first intermediate layer 506A and a second intermediate layer 506B. In some embodiments the first intermediate layer 506A is configured to physically and chemically separate the fifth pharmaceutical layers 502A and 502B. In some embodiments the second intermediate layer 506B is configured to physically and chemically separate the fifth pharmaceutical layers 502A and 502B. The first intermediate layer 506A and the second intermediate layer 506B each comprise one or more formulations configured to dissolve in vivo.

Figure 6:
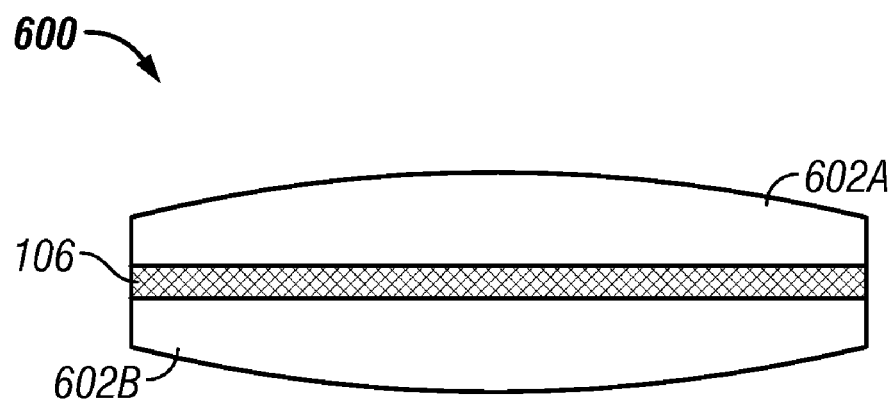
FIG. 6 illustrates a sixth embodiment of a layered pharmaceutical formulation with lenticular shaped layers.

FIG. 6 illustrates an embodiment of a sixth layered pharmaceutical formulation 600. The sixth pharmaceutical formulation 600 includes, but is not limited to sixth pharmaceutical layers 602A and 602B and an intermediate layer 106. The sixth pharmaceutical formulation 600 is configured in a lenticular shape, wherein each pharmaceutical layer 602A and 602B comprises a single convex shape.

Pharmaceutical layers may be configured in various shapes. For example, pharmaceutical layers may be configured in elliptical shapes, spherical shapes, oblong shapes, square shapes or flat shapes. In some embodiments pharmaceutical formulations are combined with fillers or excipients and placed in tablets, granules or capsules for later administration. In some embodiments the tablets are configured in spherical, elliptical, lenticular or capsule shapes.

Figure 7:
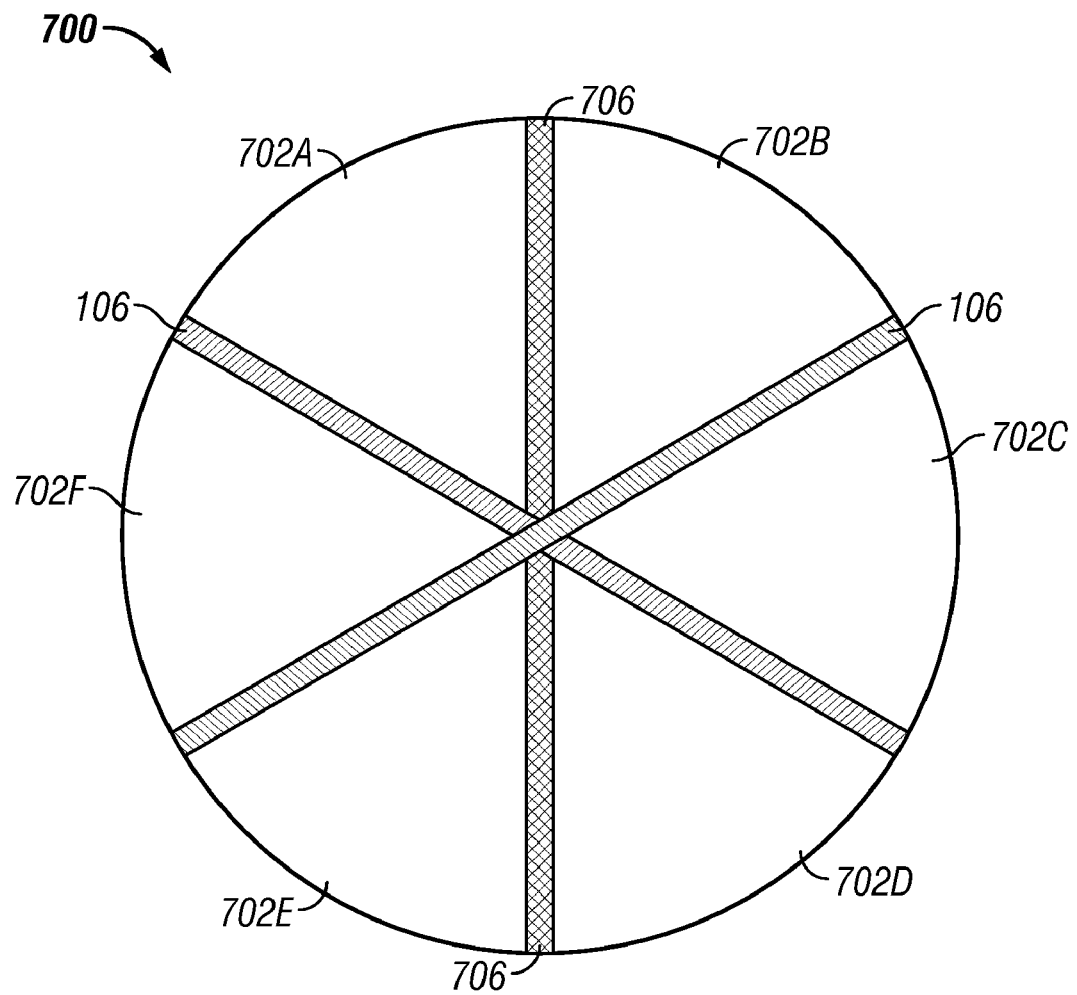
FIG. 7 illustrates a seventh embodiment of a layered pharmaceutical formulation.

FIG. 7 illustrates another embodiment of a seventh layered pharmaceutical formulation 700. The seventh pharmaceutical formulation 700 includes, but is not limited to seventh pharmaceutical layers 702A, 702B, 702C, 702D, 702E and 702F. Each seventh pharmaceutical layer 702A, 702B, 702C, 702D, 702E and 702F comprises one or more pharmaceutical compositions. Each seventh pharmaceutical layer 702A, 702B, 702C, 702D, 702E and 702F is in a wedge shape. The seventh pharmaceutical formulation 700 additionally comprises an intermediate layer 106 disposed between seventh pharmaceutical layers 702B, 702C and 702D and also between seventh pharmaceutical layers 702A, 702F and 702E. As described above the intermediate layer 106 is configured to dissolve in vivo upon contact with a certain type of bodily fluid. The seventh pharmaceutical formulation 700 additionally comprises a special intermediate layer 706 disposed between seventh pharmaceutical layers 702A and 702B and between seventh pharmaceutical layers 702D and 702E. The special intermediate layer 706 is configured to dissolve under bodily conditions different than those conditions that dissolve intermediate layer 106. Upon dissolution of the special intermediate layer 706, the seventh pharmaceutical layers 702A and 702B and the seventh pharmaceutical layers 702D and 702E are left substantially intact.

For example, if intermediate layer 106 were configured to dissolve under the acidic conditions of the stomach in a human patient, special intermediate layer 706 may be configured to dissolve only after the pharmaceutical formulation 700 reaches the duodenum. In some embodiments at least one of the pharmaceutical layers comprises an enteric coating.

Manufacture of Pharmaceutical Formulations

As noted above, pharmaceutical formulations may be configured in various shapes and sizes for ease of administration to a patient. Manufacture of pharmaceutical formulations configured in tablets comprises steps known in the art. For example, tablets may be prepared through wet-granulation, dry-granulation or direct compression. Layered pharmaceutical formulations may be configured in tablet form in a similar manner. To manufacture each pharmaceutical layer, one or more drugs are obtained in, for example, a crystalline, amorphous or powdered form, and mixed with or without diluents and/or excipients into a solid with pressure. The solid pharmaceutical layer is added with other pharmaceutical layers and/or intermediate layers and configured in a desired tablet geometry with pressure.

In some embodiments pharmaceutical formulations include, but are not limited to, one or more of polyvinylpyrrolidine (polyvinylpyrrolidone), hydroxypropyl cellulose (HPC), hydroxypropylmethyl cellulose (HPMC), methyl cellulose (MC), vinyl acetate/crotonic acid copolymers, methacrylic acid copolymers (Eudragit), maleic anhydride/methyl vinyl ether copolymers.

In some embodiments pharmaceutical formulations include, but are not limited to controlled-release formulations. In some embodiments the controlled-release formulations include, but are not limited to sustained-release formulations.

Pharmaceutical Formulations to Treat Obesity

In some embodiments the layered pharmaceutical formulation may be used to treat obesity. Obesity is a disorder characterized by the accumulation of excess fat in the body. Obesity has been recognized as one of the leading causes of disease and is emerging as a global problem. Increased instances of complications from obesity, such as hypertension, non-insulin-dependent diabetes mellitus, arteriosclerosis, dyslipidemia, certain forms of cancer, sleep apnea and osteoarthritis, have been related to increased instances of obesity in the general population.

Prior to 1994, obesity was generally considered a psychological problem. The discovery of the adipostatic hormone leptin in 1994 brought forth the realization that in certain cases, obesity may have a biochemical basis. The corollary to this realization was the idea that treatment of obesity may be achieved by chemical approaches. Since then, a number of such chemical treatments have entered the market.

Various methods of affecting weight loss, suppressing appetite and/or treating an obesity-related condition in a patient involve administering certain drugs or combinations thereof. For example, a number of references disclose the administration of certain weight loss formulations that include an anticonvulsant, an opioid antagonist and/or a norepinephrine reuptake inhibitor (NRI) to a patient in need thereof to affect weight loss. See, for example, U.S. Patent Application Publication Nos. 2004/0033965; 2004/0198668; 2004/0254208; 2005/0137144; 2005/0143322; 2005/0181070; 2005/0215552; 2005/0277579; 2006/0009514; 2006/0142290; 2006/0160750 and 2006/0079501, all of which are hereby incorporated by reference in their entireties. Weight gain has been a major concern with certain of the newer antidepressants, particularly, with paroxetine (PAXIL® PAXIL CR®) and mirtazapine (Fava, J. Clin. Psych. 61 (suppl. 11):37-41 (2000); Carpenter et al, J. Clin. Psych. 60:45-49 (1999); Aronne et al, J. Clin. Psych. 64 (suppl. 8):22-29 (2003), both of which are incorporated by reference herein in their entirety).

Other descriptions of bupropion, zonisamide, controlled-release zonisamide and combinations thereof are disclosed in U.S. Provisional Patent Application Nos. 60/740,034, filed on Nov. 28, 2005; 60/832,110, filed on Jul. 19, 2006; 60/835,564, filed on Aug. 4, 2006; and U.S. patent application Ser. NO. 11/194,201 entitled COMBINATION OF BUPROPION AND A SECOND COMPOUND FOR AFFECTING WEIGHT LOSS, filed on Aug. 1, 2005; all of which are hereby incorporated by reference in their entireties.

For methods of administering pharmaceutical compositions useful for affecting weight loss, suppressing appetite and/or treating obesity-related conditions in individuals controlled-release formulations help to suppress some if not all of the negative side effects that may arise from administration of such medication. Even in controlled-release formulations, however, the administration of certain anticonvulsants or opioid receptor antagonists at a full dosage may initially incur severe adverse side effects. Thus, at least initially, patients may be unable to tolerate a full dosage of the prescribed drug, which may include, but is not limited to an anticonvulsant or an opioid receptor antagonist. This intolerance may lead to more severe side effects and/or premature abandonment of the medication and/or the treatment program.

Administering combinations of drugs, for example, a combination including, but not limited to an anticonvulsant or an opioid receptor antagonist in combination with an antidepressant may enhance the ability of the anticonvulsant to affect weight loss, but does not necessarily eliminate the initial adverse side effects that may accompany the administration of the anticonvulsant or the opioid receptor antagonist. In some embodiments a system comprises a layered pharmaceutical for minimizing side effects during treatment of obesity. In some embodiments a method comprises administering a layered pharmaceutical formulation comprising an anticonvulsant or the opioid receptor antagonist to affect weight loss while minimizing or eliminating the initial adverse side effects on the patient.

Thus, some preferred embodiments, the layered pharmaceutical formulation is useful for the treatment of obesity and/or for affecting weight loss. Some preferred embodiments comprise at least one of an antidepressant and an anticonvulsant. Other preferred embodiments comprise at least one of an antidepressant and an opioid receptor antagonist. Other preferred embodiments comprise at least one of an anticonvulsant and an opioid receptor antagonist. Other preferred embodiments comprise at least one of an anticonvulsant and an ant diabetic.

Antidepressants and Psychotherapeutics

In some embodiments an antidepressant comprises a dopamine reuptake inhibitor or receptor antagonist. Examples of dopamine reuptake inhibitors include, but are not limited to phentermine and pharmaceutically acceptable salts or prodrugs thereof. Examples of dopamine receptor antagonists include, but are not limited to haloperidol, ocaperidone, risperidone, olanzapine, quetiapine, amisulpride, and pimozide and pharmaceutically acceptable salts or prodrugs thereof. In some embodiments the antidepressant comprises a norepinephrine reuptake inhibitor. Examples of norepinephrine reuptake inhibitors include, but are not limited to bupropion, thionisoxetine, atomoxetine and reboxetine and pharmaceutically acceptable salts or prodrugs thereof. Other embodiments include, but are not limited to those in which the antidepressant is a dopamine agonist. Dopamine agonists available on the market include cabergoline, amantadine, lisuride, pergolide, ropinirole, pramipexole, and bromocriptine. In some embodiments the antidepressant comprises a serotonin reuptake inhibitor. Examples of serotonin reuptake inhibitors include, but are not limited to fluoxetine and pharmaceutically acceptable salts or prodrugs thereof Throughout the disclosure of the present specification the term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the disclosure with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the disclosure with a base to form a salt such as ammonium salt, an alkali metal salt such as a sodium or a potassium salt, an alkaline earth metal salt such as a calcium or a magnesium salt, a salt of organic bases such as dicyclohexylamine, N-methyl-D-glucamine, tris(hydroxymethyl) methylamine and salts thereof with amino acids such as arginine, lysine and the like.

The term "prodrug" refers to an agent that is converted into the parent drug in vivo. Prodrugs are often useful because, in some situations, they are easier to administer than the parent drug. They can, for instance, be bioavailable by oral administration whereas the parent is not. The prodrug can also have improved solubility in pharmaceutical compositions over the parent drug or can demonstrate increased palpability or be easier to formulate.

An example, without limitation, of a prodrug would be a compound of the present disclosure which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to provide the active moiety.

Bupropion, whose chemical name is (±)-1-(3-chlorophenyl)-2-[(1,1-dimethylethyl)amino]-1-propanone, is the active ingredient in the drugs marketed as ZYBAN® and WELLBUTRIN®, and is usually administered as a hydrochloride salt. Throughout the present disclosure, whenever the term "bupropion" is used, it is understood that the term encompasses bupropion as a free base, or as a physiologically acceptable salt thereof, or as a bupropion metabolite or salt thereof.

The metabolites of bupropion suitable for inclusion in the methods and compositions described herein include the erythro- and threo-amino alcohols of bupropion, the erythro-amino diol of bupropion, and morpholinol metabolites of bupropion. In some embodiments, the metabolite of bupropion is (±)-(2R*,3R*)-2-(3-chlorophenyl)-3,5,5-trimethyl-2-morpholinol. In some embodiments the metabolite is (−)-(2R*,3R*)-2-(3-chlorophenyl)-3,5,5-trimethyl-2-morpholinol, while in other embodiments, the metabolite is (+)-(2S,3S)-2-(3-chlorophenyl)-3,5,5-trimethyl-2-morpholinol. Preferably, the metabolite of bupropion is (+)-(2S,3S)-2-(3-chlorophenyl)-3,5,5-trimethyl-2-morpholinol, which is known by its common name of radafaxine. The scope of the present disclosure includes the above-mentioned metabolites of bupropion as a free base or as a physiologically acceptable salt thereof. Controlled-release bupropion formulations of bupropion are known in the art. For example, U.S. Pat. No. 6,905,708 discloses a once-daily dosage configured to deliver bupropion in vivo over a 6 to 12 hour period.

Olanzapine, whose chemical name is 2-methyl-4-(4-methyl-1-piperazinyl)-10H-thieno[2,3-b][1,5]benzodiazepine, is used as a psychotherapeutic agent primarily for the treatment of schizophrenia, acute manic episodes in bipolar disorder acute, maintenance treatment in bipolar disorder and agitation associated with both these disorders. Throughout the present disclosure, whenever the term "olanzapine" is used, it is understood that the term encompasses olanzapine as a free base, or as a physiologically acceptable salt thereof, or as a olanzapine metabolite or salt thereof.

Olanzapine displays linear kinetics. Its elimination half-life ranges from 21 to 54 hours. Steady state plasma concentrations are achieved in about a week. Olanzapine undergoes extensive first pass metabolism and bioavailability is not affected by food.

The psychotherapeutic agent may be selected from the group consisting of mirtazapine, setiptiline, paroxetine, venlafaxine, olanzapine, bupropion, risperidone, lamotrogine, risperidone, a lithium salt, valproic acid, and pharmaceutically acceptable salts or prodrugs thereof. In some embodiments the psychotherapeutic agent is an antidepressant, an antimigrane, an antibipolar, an antimania drug, a mood stabilizer, or an antiepileptic. Examples of antidepressants include paroxetine, mirtazapine, and bupropion. Examples of antibipolar drugs include lithium, valproate, carbamezepine, oxycarbamezepine, lamotrogine, tiagabine, olanzapine, clozapine, risperidone, quetiapine, aripiprazole, ziprasidone, and benzodiazepines. Also included are pharmaceutically acceptable salts or prodrugs of these drugs, extended release or controlled release formulations of the above drugs, as well as combinations of the above drugs.

Fluoxetine is a selective serotonin reuptake inhibitor (SSRI), whose chemical name is N-methyl-3-phenyl-3-[4-(trifluoromethyl)phenoxy]-propan-1-amine, is used primarily for the treatment of depression (including pediatric depression), obsessive-compulsive disorder (in both adult and pediatric populations), bulimia nervosa, panic disorder, premenstrual dysphoric disorder, hypochondriasis and body dysmorphic disorder. Throughout the present disclosure, whenever the term "fluoxetine" is used, it is understood that the term encompasses fluoxetine as a free base, or as a physiologically acceptable salt thereof, or as a fluoxetine metabolite or salt thereof.

Fluoxetine has a bioavailability of approximately 72%, and peak plasma concentrations are reached in 6 to 8 hours. It is highly bound to plasma proteins, mostly albumin. Its elimination half-life ranges from 1 to 3 days—after a single dose—to 4 to 6 days (after long-term use) in healthy adults, and is prolonged in those with liver disease. The half-life of norfluoxetine is longer (16 days after long-term use). Complete excretion of the drug may take several weeks.

The SSRI can be selected from fluoxetine, fluvoxamine, sertraline, paroxetine, citalopram, escitalopram, sibutramine, duloxetine, and venlafaxine, and pharmaceutically acceptable salts or prodrugs thereof. In some embodiments, the SSRI is fluoxetine or a pharmaceutically acceptable salt or prodrug thereof.

Fluoxetine has a physiological half life of about 24 hours, whereas that of naltrexone is about 1.5 hours. However their metabolites may demonstrate half-lives in excess of 24 hours.

Thus, in some cases, it may be beneficial to administer one dose of fluoxetine per day in conjunction with two or three or more doses of naltrexone throughout the day. Naltrexone may also be in a time-release formulation where the dose is administered once a day, but naltrexone gradually enters the blood stream throughout the day, or in the course of a 12 hour period.

Symptoms of the obsessive compulsive disorders are inhibited in individuals being administered fluoxetine and naltrexone. Adverse events associated with the obsessive compulsive disorders are reduced in individuals being administered fluoxetine and naltrexone. The effects of administration of both fluoxetine and naltrexone on obsessive compulsive disorder are synergistic compared to effects of those expected by administration of fluoxetine and naltrexone alone.

Newer generation antidepressants include selective serotonin reuptake inhibitors (e.g., fluoxetine, fluvoxamine, sertraline, paroxetine, citalopram, and escitalopram), venlafaxine, duloxetine, nefazodone, mianserin setiptiline, viqualine trazodone, cianopramine, and mirtazapine.

Phentermine is an example of a dopamine reuptake inhibitor with a chemical name 2-methyl-1-phenylpropan-2-amine and 2-methyl-amphetamine. Throughout the present disclosure, whenever the term "phentermine" is used, it is understood that the term encompasses phentermine as a free base, or as a physiologically acceptable salt thereof, or as a phentermine metabolite or salt thereof.

Antidiabetic

In some embodiments an antidiabetic includes, but is not limited to a biguanide, glucosidase inhibitor, insulin, meglitinide, sulfonylurea or a thiazolidinedione. In some embodiments a biguanide comprises metformin hydrochloride. In some embodiments a glucosidase inhibitor includes, but is not limited to acarbose and miglitol. Examples of insulin include, but are not limited to human insulin, pork insulin, beef insulin, beef-pork insulin, insulin from different sources such as recombinant DNA and animal sources, as well as regular, NPH, and LENTE® types of insulin. Other examples of insulin include, but are not limited to mixtures of the various forms of insulin (e.g. NPH and regular human and pork insulin). Other examples of insulin include mixtures of Insulin Lispro Protamine and Insulin Injection (rDNA origin), a 50/50 (or a 70/30) mixture of Human Insulin Isophane Suspension and Human Insulin Injection, a 70/30 mixture of NPH Human Insulin Isophane Suspension and Human Insulin Injection (rDNA), insulin glargine, insulin lispro, insulin aspart, as well as insulin mixed with other ingredients such as zinc crystals or in a phosphate buffer. Insulin may be from *Saccharomyces cerevisiae* or other sources. Examples of meglitinides include, but are not limited to nateglinide and repaglinide. Examples of sulfonylureas include, but are not limited to glimepiride, glyburide, glibenclamide, gliquidone, gliclazide, chlorpropamide, tolbutamide, tolazamide and glipizide. Examples of thiazolidinediones include, but are not limited to rosiglitazone and pioglitazone. Also included are extended release formulations of the above drugs, as well as combinations of the above drugs and pharmaceutically acceptable salts or prodrugs thereof.

As mentioned above, in certain embodiments, the antidiabetic is metformin. Metformin, whose chemical name is 1-(diaminomethylidene)-3,3-dimethyl-guanidine, is often used in the treatment of diabetes mellitus type 2, especially when accompanied obesity and insulin resistance. Metformin has also been proven to reduce the cardiovascular complications of diabetes.

Anticonvulsants

In some embodiments, the anticonvulsant is selected from the group including, but not limited to zonisamide, topiramate, nembutal, lorazepam, clonazepam, clorazepate, tiagabine, gabapentin, fosphenytoin, phenytoin, carbamazepine, balproate, felbamate, lebetiracetam, oxcarbazepine, lamotrigine, methsuximide and ethosuxmide.

Zonisamide is a marketed anticonvulsant indicated as adjunctive therapy for adults with partial onset seizures. Without being bound by any particular theory, it is believed that the mechanism of antiepileptic activity appears to be: (1) sodium-channel blocking; and (2) reduction of inward T-type calcium occurrence. In addition, zonisamide binds to the GABA/benzodiazepine receptor complex without producing change in chloride flux. Further, zonisamide facilitates serotonergic and dopaminergic neurotransmission and possesses a weak inhibitory effect on carbonic anhydrase.

Zonisamide has been shown to cause significant weight loss (comparable to marketed weight loss medications) in patients presenting primary obesity. It has been postulated that the affect of zonisamide on the CNS concentration of serotonin, dopamine and carbonic anhydrase is responsible for this effect. There is evidence that zonisamide increases serotonin and dopamine synthesis rates herein. There is further evidence suggesting that zonisamide stimulates dopamine $D_2$ receptors.

Zonisamide can be formulated in a controlled- or sustained-release tablet or gel form. This allows a patient newly prescribed zonisamide to ramp up the dosage level over a period of several days. This increase in dosage form allows the patient to avoid some of the negative side effects that have been exhibited during the initial administration of zonisamide to a patient. Some of these initial side effects include a shock to the body. Although patients who start with a full dose of zonisamide will become acclimated to the dosage over a period of time, the negative side effects accompanying the initial shock to the body can be avoided with a method wherein dosages are increased over a period of several days.

In a pharmaceutical composition with a drug such as bupropion, a method of administering sustained-release zonisamide in a layered tablet can reduce shock to the body while maximizing bioavailability, and thus have a maximum effect for prevention of weight gain and/or treatment of obesity.

Although the exact dosages will be determined on a drug-by-drug basis, in most cases some generalizations regarding the dosage can be made. Some descriptions of appropriate unit dosages of drugs including, but not limited to bupropion, zonisamide, controlled-release zonisamide and combinations thereof are disclosed in U.S. Provisional Patent Application No. 60/740,034 entitled CONTROLLED RELEASE FORMULATION OF ZONISIMIDE, filed on Nov. 28, 2005; and U.S. patent application Ser. No. 11/194,202 entitled COMBINATION OF BUPROPION AND A SECOND COMPOUND FOR AFFECTING WEIGHT LOSS, filed on Aug. 1, 2005; which are hereby incorporated by reference in their entireties, and U.S. Patent Publication Nos. 2005/0215552 and 2006/0079501 mentioned previously.

In some embodiments the anticonvulsant is a γ-amino butyric acid (GABA) inhibitor, a GABA receptor antagonist or a GABA channel modulator. By "GABA inhibitor" it is meant a compound that reduces the production of GABA in the cells, reduces the release of GABA from the cells, or reduces the activity of GABA on its receptors, either by preventing the binding of GABA to GABA receptors or by minimizing the effect of such binding. The GABA inhibitor may be a 5-HT1b agonist or another agent that inhibits the activity of NPY/AgRP/GABA neurons. In addition, the GABA inhibitor may suppress the expression of the AgRP gene, or the GABA inhibitor may suppress the production or release of AgRP. It is, however, understood that a 5-HT1b agonist may inhibit the NPY/AgRP/GABA neuron (and therefore activate pro-opiomelanocortin (POMC) neurons) without acting as an inhibitor of the GABA pathway.

In certain other embodiments the GABA inhibitor increases the expression of the POMC gene. In some of these embodiments, the GABA inhibitor increases the production or release of POMC protein. In certain other of these embodiments, the GABA inhibitor increases the activity on POMC expressing neurons.

In some embodiments, the GABA inhibitor is topiramate. Topiramate, whose chemical name is 2,3:4,5-Bis-O-(1-methylethylidene)-beta-D-fructopyranose sulfamate, is often used to treat epilepsy, Lennox-Gastaut syndrome (a disorder causing seizures and developmental delays), neuropathic pain, bipolar disorder, obesity including reduction of binge eating, alcoholism, Post Traumatic Stress Disorder, infantile spasm, bulimia nervosa, or obsessive-compulsive disorder or to assist smoking cessation or prevent migraines. Generally, initial doses of topiramate are low and increased in slow steps. The usual initial dose is 25 to 50 mg daily in 2 single doses. Recommended increments vary, but are usually between 25 mg and 50 mg every 1 or 2 weeks. Common doses for maintenance treatment include, but are not limited to doses of approximately 100 to 200 mg daily.

Opioid Receptor Antagonists

In certain embodiments the opioid antagonist antagonizes a μ-opioid receptor (MOP-R) in a mammal. The mammal may be selected from the group including, but not limited to mice, rats, rabbits, guinea pigs, dogs, cats, sheep, goats, cows, primates, such as monkeys, chimpanzees, and apes, and humans.

In some embodiments the opioid antagonist is selected from the group including, but not limited to alvimopan, norbinaltorphimine, nalmefene, naloxone, naltrexone, methylnaltrexone, and nalorphine, and pharmaceutically acceptable salts or prodrugs thereof.

In other embodiments, the opioid antagonist is a partial opioid agonist. Compounds of this class have some agonist activity at opioid receptors. However, because they are weak agonists, they function as de-facto antagonists. Examples of partial opioid agonists include, but are not limited to pentacozine, buprenorphine, nalorphine, propiram, and lofexidine.

Naltrexone (17-(cyclopropylmethly)-4,5α-epoxy-3,14-dihydroxymorphinan-6-one), shown below, is an opioid receptor antagonist used primarily in the management of alcohol dependence and opioid dependence. μ-subtype selective opioid antagonists such as naltrexone are also of considerable current interest as agents for the treatment of obesity (Glass, M. J.; Billington, C. J.; Levine, A. S. *Neuropeptides* 1999, 33, 350) and CNS disorders (Reneric, J. P.; Bouvard, M. P. *CNS Drugs* 1998, 10, 365).

It is marketed as its hydrochloride salt, naltrexone hydrochloride, under the trade name REVIA™. REVIA™ is an immediate release formulation of naltrexone, with 100 mg strength. The maximum serum concentration of immediate release naltrexone is reached very rapidly, typically a $T_{max}$ of approximately 1 hour. Immediate release naltrexone can induce side effects such as nausea, which is attributable to the maximum blood plasma concentration levels ($C_{max}$).

An oral dosage form of naltrexone that is able to effect naltrexone release at a rate sufficiently slow to ameliorate side effects, yet sufficiently fast to achieve good bioavailability would provide a significant improvement in dosing compliance and convenience. Likewise, an improved dosage form which lowered the incidence of gastrointestinal side-effects would also be of significant value.

In some embodiments, oral dosage forms of naltrexone are effective to provide an AUC between about 75% to about 125% of 50 mg immediate release naltrexone tablets. In some embodiments oral dosage forms of naltrexone provide an amount of a retardant excipient that is effective to provide a $C_{max}$ that is less than or equal to about 80% of the $C_{max}$ of 50 mg immediate release naltrexone tablets.

Formulations of controlled- or sustained-release naltrexone have been disclosed in U.S. Provisional Patent Application Ser. No. 60/811,251, filed Jun. 5, 2006, which is hereby incorporated by reference in its entirety. In some embodiments, oral dosage forms of naltrexone are effective to provide an AUC between about 75% to about 125% of 50 mg immediate release naltrexone tablets. In some embodiments oral dosage forms of naltrexone comprise an amount of a retardant excipient that is effective to provide a $C_{max}$ that is less than or equal to about 80% of the $C_{max}$ of 50 mg immediate release naltrexone tablets.

Those skilled in the art informed by the guidance provided herein can formulate oral dosage forms described herein. For example, one skilled in the art could formulate an oral dosage form that includes, but is not limited to an amount of naltrexone effective to provide an AUC between about 75% to about 125% of 50 mg immediate release naltrexone tablets, and an amount of an appropriate retardant excipient effective to provide a $C_{max}$ that is less than or equal to about 80% of the $C_{max}$ of 50 mg immediate release naltrexone tablets. Further, given the guidance provided herein, the skilled artisan could formulate an oral dosage form having a pharmacodynamic profile characterized by coverage of greater than or equal to 80% of the opioid receptors in the hypothalamus.

EXAMPLES

Below are found specific examples of pharmaceutical compositions that may be formed into layered pharmaceutical formulations of the present disclosure.

TABLE 1

Formulations for Sustained-Release (SR) Tablets Containing Bupropion

| Ingredient | 70 mg Bupropion SR Amount per Tablet | 90 mg Bupropion SR Amount per Tablet |
|---|---|---|
| Bupropion HCL, USP | 70.0 mg | 90.0 mg |
| Microcrystalline Cellulose, NF (Avicel PH 101) | 173.3 mg | 153.3 mg |
| Hydroxypropyl Cellulose, NF (Klucel HXF) | 56.7 mg | 56.7 mg |
| Cysteine HCL, NF | 12.5 mg | 12.5 mg |
| Magnesium Stearate, NF | 2.5 mg | 2.5 mg |
| Tablet Weight | 315.0 mg | 315.0 mg |

TABLE 2

Formulations for Sustained-Release (SR) Tablets Containing Zonisamide

| Ingredient | 30 mg Zonisamide SR Amount per Tablet | 60 mg Zonisamide SR Amount per Tablet | 90 mg Zonisamide SR Amount per Tablet |
|---|---|---|---|
| Zonisamide | 30 mg | 60 mg | 90 mg |
| Klucel | 110 mg | 35 mg | 35 mg |
| Lactose | 55 mg | 70 mg | 60 mg |
| Colloidal Silicon Dioxide, NF | 2 mg | 2 mg | 2 mg |
| Cross Povidone | 20 mg | 14 mg | 14 mg |
| Magnesium Stearate, NF | 6 mg | 6 mg | 6 mg |
| Microcrystalline Cellulose, NF | 127 mg | 163 mg | 143 mg |

TABLE 3

Formulations for Sustained-Release (SR) Tablets Containing Naltrexone

| Ingredient | Percent per Tablet "12.5% HPMC" SR-Fast | Percent per Tablet "30% HPMC" SR-Medium | Percent per Tablet "44% HPMC" SR-Slow |
|---|---|---|---|
| Naltrexone (5 mg) | 6.667 | 6.667 | 6.667 |
| Hydroxypropylmethyl Cellulose (Methocel K15 Premium) | 10.000 | 30.000 | 44.333 |
| Common QBQ01 Placebo Granulation | 81.733 | 61.833 | 47.500 |
| Colloidal Silicon Dioxide, NF (Cab-O-Sil M5P) | 1.000 | 0.500 | 1.000 |
| Sodium Edetate | 0.1 | — | — |
| Magnesium Stearate, NF, Ph.Eur. (Vegetable Source) (Grade 905-G) | 0.500 | 6.667 | 0.500 |
| | 100.000 | 100.000 | 100.000 |

Thus, as illustrated in Tables 1-3 above, embodiments of pharmaceutical formulations may comprise controlled-release (e.g., sustained release in the illustrated embodiments) formulations of bupropion, zonisamide and/or naltrexone. In one embodiment, a layered pharmaceutical formulation is a tablet comprising a first layer comprising a controlled-release zonisamide and a second layer comprising a bupropion. In another embodiment a layered pharmaceutical formulation is a tablet comprising a first layer comprising a controlled-release naltrexone and a second layer comprising a controlled-release bupropion. In some embodiments the first layer and the second layer are separated by an intermediate layer comprising lactose or other suitable fast-dissolving ingredient.

The oral dosage forms of pharmaceutical formulations can, if desired, be presented in a unit dosage package which may contain one or more unit dosage forms containing the active ingredient. The unit dosage package may for example comprise metal or plastic foil, such as a blister pack. The unit dosage package may be accompanied by instructions for administration. The unit dosage package may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the disclosure formulated in a compatible pharmaceutical carrier may also be prepared, placed in an appropriate container, and labeled for treatment of an indicated condition.

Novel methods and systems for administering weight loss medications are described in co-pending application entitled METHODS FOR ADMINISTERING WEIGHT LOSS MEDICATIONS filed on the same day as the present application, which is hereby incorporated by reference in its entirety.

In some embodiments, the weight loss medications are provided at least once, twice or three times a day for a set period, which can be at least, at least about, less than, less than about, equal to or between any range within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, at least about, less than, less than about, equal to or between any range within of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, at least about, less than, less than about, equal to or between any range within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. The amount of drug in any pharmaceutical formulation described herein includes, but is not limited to amounts of at least, at least about, less than, less than about, equal to or between any range within 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 250, 300, 350, 400, 450, 500, 550, 600, 650, 700, 750, 800, 850, 900, 950, 1000, 1500, 2000, 3000, 4000 or 5000 mg.

In one embodiment a layered pharmaceutical formulation for the administration of two or more active pharmaceutical ingredients comprises a first pharmaceutical layer comprising a first active pharmaceutical ingredient, a second pharmaceutical layer comprising a second active pharmaceutical ingredient and at least one intermediate layer disposed between the first and the second pharmaceutical layers, wherein the at least one intermediate layer is configured to dissolve in vivo to thereby leave the first and the second pharmaceutical layers substantially intact.

In some embodiments each of the first and the second pharmaceutical layers comprises a dissolution profile substantially similar to a singularly compressed tablet of a similar composition. In some embodiments each of the first and the second pharmaceutical layers comprises a different pharmaceutical composition. In some embodiments at least one of the first and the second pharmaceutical layers comprises a controlled-release pharmaceutical composition. In some embodiments the controlled-release pharmaceutical composition comprises a sustained release pharmaceutical composition.

In some embodiments at least one of the first and the second pharmaceutical layers comprises zonisamide. In some embodiments the zonisamide comprises a controlled-release zonisamide. In some embodiments the controlled-release zonisamide comprises a sustained-release zonisamide. In some embodiments at least one of the first and the second pharmaceutical layers comprises bupropion. In some embodiments the bupropion comprises a controlled-release bupropion. In some embodiments the controlled-release bupropion comprises a sustained-release bupropion. In some embodiments at least one of the first and the second pharmaceutical layers comprises naltrexone. In some embodiments at least one of the first and the second pharmaceutical layers comprises fluoxetine.

In some embodiments at least one of the first and the second pharmaceutical layers comprises olanzapine. In some embodiments at least one of the first and the second pharmaceutical layers comprises an antidiabetic. In some embodiments the antidiabetic comprises metformin. In some embodiments at least one of the first and the second pharmaceutical layers comprises topiramate. In some embodiments at least one of the first and the second pharmaceutical layers comprises phentermine. In some embodiments the at least one intermediate layer comprises at least one of a monosaccharide sugar, a disaccharide sugar, or a starch. In some embodiments the at least one intermediate layer comprises lactose.

In one embodiment a method for affecting weight loss, suppressing appetite and/or treating an obesity-related condition in a patient comprises providing a first dosage of the layered pharmaceutical formulation to a patient in need thereof on a first day and providing a second dosage of the layered pharmaceutical formulation to the patient on a second day. In some embodiments the first dosage is greater than the second dosage. In some embodiments the second dosage is greater than the first dosage.

In one embodiment a method for treating an obesity related condition in a patient comprises identifying a patient with an obesity related condition or at risk of an obesity related condition comprises providing a first dosage of the layered pharmaceutical formulation of claims 1 to the patient on a first day and providing a second dosage of the layered pharmaceutical formulation to the patient on a second day. In some embodiments the first dosage is different than the second dosage. In some embodiments the second dosage is greater than the first dosage.

In one embodiment use of a first compound and a second compound in the formulation of a medicament for affecting weight loss, suppressing appetite or treating an obesity-related condition, wherein the medicament comprises a layered pharmaceutical formulation of the present invention.

It will be appreciated by those skilled in the art that various modifications and changes can be made without departing from the scope of the disclosure. Such modifications and changes are intended to fall within the scope of the disclosure, as defined by the appended claims.

What is claimed is:

1. A layered pharmaceutical formulation for the administration of two or more active pharmaceutical ingredients comprising:
    a first pharmaceutical layer comprising between about 2 mg and about 35 mg of sustained-release naltrexone;
    a second pharmaceutical layer comprising between about 50 mg and about 200 mg of sustained-release bupropion; and
    an intermediate layer disposed between said first and said second pharmaceutical layers,
    wherein said intermediate layer comprising a monosaccharide sugar or a disaccharide sugar is configured to rapidly dissolve in vivo, and thereby leave said first and said second pharmaceutical layers substantially intact but physically separated, and
    wherein the dissolution profile of naltrexone in the pharmaceutical formulation is substantially the same as a single compressed tablet of naltrexone having the same size and shape as said first pharmaceutical layer, and wherein the dissolution profile of bupropion in the layered pharmaceutical formulation is substantially the same as a single compressed tablet of the same pharmaceutical composition, size and shape as said second pharmaceutical layer.

2. The layered pharmaceutical formulation of claim 1, wherein said intermediate layer comprises lactose.

3. The layered pharmaceutical formulation of claim 1, wherein the first pharmaceutical layer comprises between about 4 mg and about 10 mg of said sustained-release naltrexone.

4. The layered pharmaceutical formulation of claim 1, wherein the second pharmaceutical layer comprises between about 75 mg and about 150 mg of said sustained-release bupropion.

5. The layered pharmaceutical formulation of claim 1, wherein the second pharmaceutical layer comprises between about 85 mg and about 100 mg of said sustained-release bupropion.

6. The layered pharmaceutical formulation of claim 1, wherein said first and said second pharmaceutical layers separate in vivo in less than 1 minute.

* * * * *